(12) United States Patent
Sun

(10) Patent No.: US 11,254,754 B2
(45) Date of Patent: Feb. 22, 2022

(54) BIOCOMPATIBLE POLYSACCHARIDE HYDROGELS AND METHODS OF USAGE

(71) Applicant: Guoming Sun, Lutherville Timonium, MD (US)

(72) Inventor: Guoming Sun, Lutherville Timonium, MD (US)

(73) Assignee: Guoming Sun, Lutherville, MD (US)

( * ) Notice: Subject to any disclaimer, the term of this patent is extended or adjusted under 35 U.S.C. 154(b) by 667 days.

(21) Appl. No.: 16/067,885

(22) PCT Filed: Jan. 13, 2017

(86) PCT No.: PCT/US2017/013568
§ 371 (c)(1),
(2) Date: Jul. 3, 2018

(87) PCT Pub. No.: WO2017/124040
PCT Pub. Date: Jul. 20, 2017

(65) Prior Publication Data
US 2020/0262938 A1     Aug. 20, 2020

Related U.S. Application Data

(60) Provisional application No. 62/279,786, filed on Jan. 17, 2016.

(51) Int. Cl.
*C08B 37/02* (2006.01)
*A61L 27/20* (2006.01)
*A61L 27/52* (2006.01)
*A61L 27/54* (2006.01)

(52) U.S. Cl.
CPC .......... *C08B 37/0021* (2013.01); *A61L 27/20* (2013.01); *A61L 27/52* (2013.01); *A61L 27/54* (2013.01); *A61L 2300/414* (2013.01); *A61L 2300/428* (2013.01); *A61L 2430/34* (2013.01)

(58) Field of Classification Search
CPC ... C08B 37/0021; C08B 37/006; A61L 27/20; A61L 27/52; A61L 27/54; A61L 2300/414; A61L 2300/428; A61L 2430/34; A61L 27/58; A61L 27/60; A61P 9/14; A61P 9/00; A61P 43/00; A61P 27/02; A61P 21/00; A61P 19/04; A61P 19/00; A61P 17/02; A61P 17/00; A61P 11/00; A61P 1/16; A61P 1/04; A61P 1/02; C08L 5/00; C08L 5/02
See application file for complete search history.

(56) References Cited

PUBLICATIONS

Haijun et al. (CN103641925A Machine translation) (Year: 2012).*
Thermes et al. ("Mucoadhesion of Copolymers and Mixtures Containing Polyacrylic Acid") Pharm Res 9, 1563-1567 (1992) (Year: 1992).*

* cited by examiner

*Primary Examiner* — Quanglong N Truong

(57) ABSTRACT

The disclosure provides hydrogel compositions comprising polysaccharides with repeat units and methods of synthesis and usage.

50 Claims, 9 Drawing Sheets

BIOCOMPATIBLE POLYSACCHARIDE HYDROGELS AND METHODS OF USAGE

CROSS-REFERENCE TO RELATED PATENT APPLICATIONS

This application claims priority under 35 U.S.C. 119(e) to U.S. Ser. No. 62/279,786, filed Jan. 17, 2016, the contents of which is incorporated herein by reference in its entirety.

FIELD

The present disclosure generally relates to the field of polysaccharide hydrogels, and their compositions, and methods of making and usage.

BACKGROUND

As the largest organ in the body, the skin conducts a wide range of functions to support and maintain human health (Schulz III et al. Annual Review of Medicine, Vol. 51, pp. 231-244, 2000; Sun et al. Nanomedicine, 2012). The skin epidermis and its appendages (e.g., hair follicle, sebaceous and sweat glands) provide a protective barrier against physical, chemical and biological pathogens and also prevent dehydration. However, full-thickness skin wounding commonly leads to non-functioning scar formation with substantial loss of skin appendages. Cutaneous scar formation can cause severe cosmetic, functional, and psychological problems. There are more than 87 million patients in the U.S. and Europe that could benefit from scar reduction therapies (Bush et al. Dermatology Research and Practice, Vol. 2010, 2010; Mak et al. Journal of Dermatological Science, Vol. 56, pp. 168-180, 2009). Despite tremendous efforts to attenuate scarring, the regeneration of perfect skin remains a challenge and highly prized goal (Martin. Science, Vol. 276, pp. 75-81, 1997), and has thus become a major aim in wound healing (Heng. International Journal of Dermatology, Vol. 50, pp. 1058-1066, 2011; Martin. Science, Vol. 276, pp. 75-81, 1997; Sun et al. JSM Regen Med, Vol. 1, p. 1007, 2013).

Traditionally, the subject of tissue engineering aims to build functional substitutes for damaged tissues in vitro and then transplant them to repair and/or restore the damaged organs. For acute deep wounds, for example, full thickness human skin equivalent would be first developed in vitro and then transplanted to patients. However, their healing outcome is far from satisfactory. In recent years, it has become well-known that various living tissues can have a staggering capacity for regeneration, such as liver, bone and skin. An emerging philosophy in tissue engineering is that rather than attempting to recreate the complexity of living tissues ex vivo, we should aim to develop synthetic materials that establish key interactions with cells in ways that unlock the body's innate powers of organization and self-repair (Place et al. Nat Mater, Vol. 8, pp. 457-470, 2009).

Hydrogels are three-dimensional hydrophilic networks that are structurally similar to natural extracellular matrix (ECM). Other than their appealing biomimetic structures, hydrogels also have unique biocompatibility, flexible methods of synthesis, a wide range of constituents, and desirable physical characteristics. They have thus been the material of choice for many applications in regenerative medicine (Slaughter et al. Advanced Materials, Vol. 21, pp. 3307-3329, 2009; Van Tomme et al. International Journal of Pharmaceutics, Vol. 355, pp. 1-18, 2008). Hydrogels can be engineered to incorporate different functionalities and protect biologically active molecules from being altered, thus they are used as intelligent drug delivery systems (DDS) (Schillemans et al. Journal of Controlled Release, Vol. 150, pp. 266-271, 2011; Van Tomme et al. Biomaterials, Vol. 26, pp. 2129-2135, 2005). Meanwhile, many biochemical and physical cues can be incorporated into hydrogel to mimic the in vivo microenvironment, thus acting as a definitive tissue regeneration template to provide an instructive environment for three-dimensional cell assembly into functional tissues or organs.

Biocompatibility is one significant consideration for the tissue-engineered scaffolds. And this consideration is important for wound healing. Excessive inflammatory cells result in fibrosis tissue formation in adults (Coolen et al. Wound Repair Regen, Vol. 18, pp. 291-301, 2010). Macrophages are important inflammation cells. Other than augmenting inflammatory responses, macrophages also stimulate new tissue formation at the proliferative stage and mediate ECM synthesis at the remodeling stage. Once injured, circulating monocytes are recruited to the wound sites, but soon differentiate into macrophages with the help of TGF-β, monocytes. Under different stimulation, macrophages can be further polarized into either pro-inflammatory macrophage (M1) or anti-inflammatory macrophage (M2). They produce both pro-inflammatory cytokines (e.g., IL-1, IL-6) and growth factors (e.g., PDGF, TGF-β, VEGF, FGF and EGF) (Barrientos et al. Wound Repair and Regeneration, Vol. 16, pp. 585-601, 2008; Delavary et al. Immunobiology, Vol. 216, pp. 753-762, 2011), thus macrophages may either initiate tissue regeneration (M2) or give rise to destruction (M1) (Brancato et al. The American Journal of Pathology, Vol. 178, pp. 19-25, 2011; Martinez et al. Front Biosci, Vol. 13, pp. 453-461, 2008). Recent studies indicate that there is a strong correlation between the macrophage response to implanted ECM scaffold materials (Brown et al. Acta Biomaterialia, Vol. 8, pp. 978-987, 2012), and a favorable M2 phenotype could encourage a constructive tissue remodeling. As such, the interplay between macrophage phenotype and ECM scaffold materials could be used to predict the outcome of wound repair, and there exists in regenerative medicine a desire of biomaterials that have great biocompatibility and can hoax macrophage into M2 phenotype. Consequently, a scaffold that causes no or less immune response is especially desirable for wound healing. Although some collagen-based scaffolds have been accepted for clinical use, increased inflammation has been observed in clinical research (Moreira Teixeira et al. Biomaterials, Vol. 33, pp. 3651-3661, 2012; Muangman et al. Journal of Trauma and Acute Care Surgery, Vol. 61, pp. 1212-1217, 2006).

It was recently demonstrated that the Dex-AE/PEGDA hydrogels promoted dermal regeneration with complete skin appendages on a third-degree burn injury in murine model. See Sun et al., *Proceedings of the National Academy of Sciences*, Vol. 108, pp. 20976-20981 (2011). The wound healing in preclinical porcine model, however, showed incomplete regeneration (Shen et al. *The Journal of investigative dermatology*, Vol. 135, pp. 2519-2529, 2015). In this formula, the polyethylene glycol (PEG) content (around 20%) causes immobilization and repels cell attachment and infiltration, which could undermine the therapeutic benefits and clinical significance of the hydrogels.

Therefore, there exists a need for more biocompatible, biodegradable hydrogels that can enhance the innate self-regenerating powers, trigger or activate different signaling pathways, and induce the proliferation, differentiation, maturation, and/or migration of stem cells to form skin structures and other functional tissues at or around the wounded regions.

SUMMARY OF THE INVENTION

One embodiment of the disclosure relates to a composition comprising, consisting essentially of, or yet further consisting of, a polysaccharide which comprises, consists essentially of, or yet further consists of a first repeat unit and a second repeat unit, wherein the first repeat unit has formula (I):

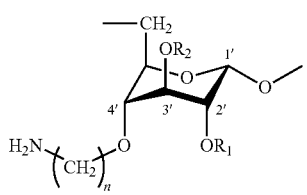

Formula (I)

wherein the second repeat unit has formula (II):

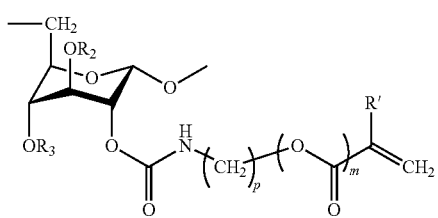

Formula (II)

wherein R1 is selected from a group consisting of hydrogen, —OCONH($CH_2$)$_p$(COO)$_m$CR'=$CH_2$, and —O($CH_2$)$_n$$NH_2$, wherein R' is hydrogen or a methyl group, n is no less than 1, m is no less than 1, and p is no less than 1; wherein R2 is selected from a group consisting of hydrogen, —OCONH ($CH_2$)$_p$(COO)$_m$CR'=$CH_2$, and —O($CH_2$)n$NH_2$, wherein R' is hydrogen or a methyl group, n is no less than 1, m is no less than 1, and p is no less than 1; wherein R3 is selected from a group consisting of hydrogen, —OCONH($CH_2$)$_p$ (COO)$_m$CR'=$CH_2$, and —O($CH_2$)n$NH_2$, wherein R' is hydrogen or a methyl group, n is no less than 1, m is no less than 1, and p is no less than 1. In some embodiment, the first repeat unit is the same as the second repeat unit.

In another aspect, the disclosure relates to methods of forming the composition into a hydrogel, comprising, consisting essentially of, or yet further consisting of, combining in a solution the composition for a sufficient period of time; and exposing the solution to UV light, wherein a crosslinked polymer network structure is formed within the composition after exposure.

In one aspect, the disclosure relates to methods of synthesizing a macromer, comprising, consisting essentially of, or yet further consisting of, reacting a first compound comprising, consisting essentially of, or yet further consisting of —($CH_2$)$_p$(COO)$_m$CR'=$CH_2$ with a hydroxyl group of a polysaccharide to give rise to a first macromer comprising, consisting essentially of, or yet further consisting of a polymerizing moiety and a hydrolytically degradable linker, where the macromer is formula II, and reacting the first macromer with a second compound comprising, consisting essentially of, or yet further consisting of —($CH_2$)$_n$$NH_2$ with a free hydroxyl group of the first macromere to form a second macromere, wherein the second macromer is formula III.

In a further embodiment, the disclosure relates to a hydrogel forming system, wherein the system comprises, consists essentially of, or yet further consists of, a polysaccharide which comprises, consists essentially of, or yet further consists of the first repeat unit of formula I and the second repeat unit of formula II, wherein at least one repeat unit having at least a polymerizing moiety; wherein the system is polymerized after exposed to UV light, thus forming a three-dimensional polymer network.

In one embodiment, the disclosure also relates to methods of attenuating scarring, which methods comprise, consist essentially of, or yet further consist of excising the scarred skin, and regenerating the skin on the scarred skin area with any one of the compositions in the disclosure. In another embodiment, the disclosure relates to methods of promoting cutaneous wound healing or dermal regeneration and skin appendage, which methods comprise, consist essentially of, or yet further consist of applying to a portion of injured skin area any one of the compositions of the disclosure.

BRIEF DESCRIPTION OF THE DRAWINGS

FIG. 2A presents the in vitro biocompatibility of dextran derived macromolecules, and FIG. 2A(i) shows the cell viability of macromers in COS7 cells after 48 hours, and FIG. 2A(ii) shows the cytotoxicity of macromers in hASC at 0.05 mg/mL culture medium. FIG. 2B shows the chemical synthesis of biocompatible DexIEME by reacting dextran with 2-isocyanatoethyl methacrylate (DexIEM) followed by ethylamine incorporation (DexIEME). Significance levels were set at: *$p<0.05$, $p<0.01$, and *$p<0.001$. Values shown are means±SD.

FIG. 3A shows the 1HNMR spectra of (i) dextran, (ii) DexIEM and (iii) DexIEME. FIG. 3B shows the FTIR spectra of (i) dextran, (ii) DexIEM and (iii) DexIEME (1&2: ~1635 cm−1; 3: ~1541 cm−1; 4: ~1535 cm−1).

FIG. 4A illustrates monocyte differentiation into macrophage followed by further polarization. FIG. 4B exemplifies the impact of macromers on (i) macrophage differentiation and further (ii) macrophage polarization into pro-inflammatory (M1) and (iii) anti-inflammatory (M2) macrophages.

FIG. 6A shows the synthesis of DexIEME hydrogel, including (i) chemical reaction under (ii) UV photocrosslinking at the presence of Irgacure 2959. FIG. 6B shows the optimization of hydrogel crosslinking, including (i) hydrogel conversion efficiency and (ii) swelling ratio under different concentrations and time.

FIG. 8A illustrates the creation of scarred skin and partial treatment with hydrogel in mouse dorsum. FIG. 8A(i) shows scar creation by third-degree burn, FIG. 8A(ii) shows partial excision of scarred skin, then FIG. 8A(iii) shows applying hydrogel to the wound area, and FIG. 8A(iv) shows the outcome of wound healing after 5 weeks. FIG. 8B shows the scarred skin excised from the third-degree burn. FIG. 8C shows the newly regenerated skin after hydrogel treatment, FIG. 8C(i) shows the representative hematoxylin and eosin (H&E) image of newly regenerated skin from the scarred skin, while the dotted lines delineate the scarred skin from burn and newly regenerated skin after hydrogel treatment, FIG. 8C(ii) shows the higher magnification of completely regenerated skin from the scar site, FIG. 8C(iii) shows the higher magnification of scarred skin from burn unchanged. Scale bars=200 µm. FIG. 8D shows the quantification of hair follicle between the newly regenerated skin and scarred skin. FIG. 8E shows the newly regenerated hair expressed in cortex (AE13), companion layer (k75) and outer root sheath (AE13/AE15). Scale bars=25 µm.

FIG. 8D was calculated based on the H&E images from these retreatment experiments.

FIG. 10A shows the creation of scarred skin and full hydrogel treatment in mouse dorsum. FIG. 10A(i) shows skin excised from third-degree burn scar, FIG. 10A(ii) shows the application of hydrogel on fully excised scar wound, FIG. 10A(iii) shows the skin regenerated after 4 weeks, FIG. 10A(iv) shows the opposite side of skin. FIG. 10B shows hydrogel regenerating complete skin structure. FIG. 10B(i) shows regenerated skin from the scar skin, while the dotted lines delineate the new skin from three different locations, while FIGS. 10B(i), 10B(ii), and 10B(iii) are the blow-up of the three locations indicating new skin formation. Scale bars=200 µm.

FIG. 11A shows the surgical procedure of full skin excision down to subcutaneous tissue, FIG. 11A(i) shows the hydrogel, FIG. 9A(ii) shows the circular wound which is 2.5 cm in diameter, FIG. 11A(iii) shows the application of hydrogel to cover the entire wound, FIG. 11A(iv) shows the wound without and with hydrogel treatment, FIG. 11(v) shows the wound healed after 10 weeks and FIG. 9A(vi) shows the wound healed after hydrogel treatment. FIG. 11B shows the representative H&E images of wound healing at different time points: (i) (ii) and (iii) are the wound without hydrogel treatment, (v)(vi) and (vii) are the hydrogel treated wound healing, and (iv) and (viii) are blowups of the control and hydrogel treated wounds, respectively. The dotted line in FIGS. 11B(ii) and 11B(vi) delineates the wound interface between the newly formed tissue and normal skin. Scale bars=200 µm.

DETAILED DESCRIPTION

Figure 1:
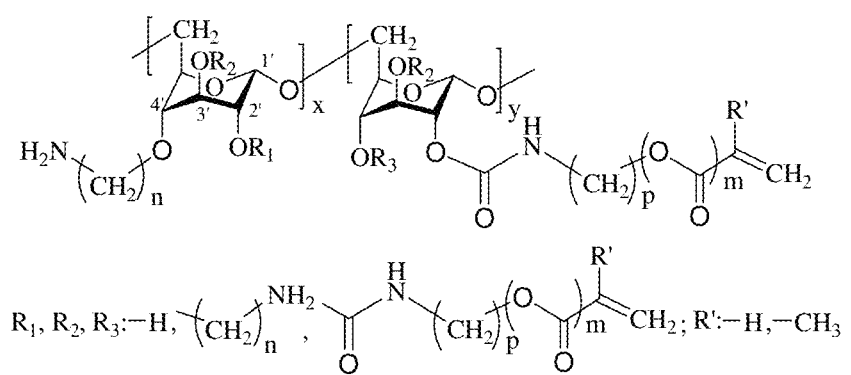
FIG. 1 shows the general chemical structures of synthesized highly biocompatible and biodegradable dextran macromers.

It is to be understood that this invention is not limited to the particular methodology, protocols, cell lines, animal species or genera, compounds, polymers, and reagents described, as such may vary. It is also to be understood that the terminology used herein is for the purpose of describing particular embodiments only and is not intended to limit the scope of the present invention, which will be limited only by the appended claims.

As used herein, the singular forms "a," "an," and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Any embodiment of any of the present methods, devices, and systems may consist of, or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only, or the alternatives are mutually exclusive, although the disclosure supports a definition that refers to only alternatives and "and/or."

Throughout this application, the term "about" is used to indicate that a value includes the standard deviation of error for the device or method being employed to determine the value.

The term "plurality," as used herein, means more than one. When a range of values is expressed, another embodiment includes from the one particular value and/or to the other particular value. All references cited herein are incorporated by reference as if each had been individually incorporated.

As used herein, the terms "treat," "treating," "treatment," "therapeutic," "regenerate," "regenerating," "regeneration" and the like refer to reducing or ameliorating a disorder and/or symptoms associated therewith. It will be appreciated that, although not precluded, treating a disorder or condition does not require that the disorder, condition or symptoms associated therewith be completely eliminated.

The term "ameliorate" is meant to reduce, decrease, suppress, attenuate, diminish, arrest, or stabilize the development or progression of a diseased or damaged skin.

The term "crosslinked composition" as used herein means a composition capable of forming a three-dimensional network, and the network may be solid or a fluid-like gel. Persons skilled in the art will generally be able to distinguish a solid hydrogel from a fluid-like hydrogel. For instance, a "solid hydrogel" is capable of maintaining its shape after crosslinking, or has sufficient mechanical properties; while a "fluid-like gel" may be incapable of maintaining its shape even after crosslinking, or has insufficient mechanical strength. However, by way of example, and not limitation, a fluid-like hydrogel may be considered a hydrogel having an increase in mechanical strength and a loose network structure.

As used herein, the term "polysaccharide" refers to polymers comprising, consisting essentially of, or yet further consisting of a backbone including mainly (at least 90%) monosaccharide repeating units and/or derivatized monosaccharide repeating units. Non-limiting examples include starches, modified starches, amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, cellulose, modified cellulose (representative examples include carboxyalkylated cellulose and carboxymethyl cellulose), oxidized polysaccharides, sulfated polysaccharides, cationic polysaccharides (such as, but not limited to, the chitosan, quaternary ammonium derivatives of polysaccharides or guanidinated polysaccharides, as described in Canadian Patent No. 2,519,417 (Berrada)), pectin, gum arabic, gum karaya, xanthan, kappa, iota or lambda carrageenans, agar-agar, alginates and a mixture thereof.

As used herein, the term "repeat unit" has the ordinary meaning understood by one of ordinary skill in the art. In some embodiments, the term "repeat unit" refers to a part of a polymer which attaches in at least two positions to another repeat unit or a terminal unit of the polymer.

As used herein, the term "hydrogel" is used herein to refer to a porous three-dimensional macromolecular network that swells in water and includes one or more monomers polymerized with or without crosslinkers. In some embodiment, the hydrogel can form without crosslinker (e.g., some embodiments in the invention). In some embodiment, the formation of hydrogel requires crosslinker, for example, the Dex-AE/PEGDA system.

As used herein, the term "crosslinker" is used herein in its conventional sense, i.e., a molecule that can form a three-dimensional network when reacted with the appropriate base monomers.

As used herein, the term "crosslinked" is used herein to refer to when the crosslinker has reacted with the base monomer molecule to form a three-dimensional network.

As used herein, the term "scaffold" refers to a three-dimensional porous polymeric structure with or without mechanical strength to support new tissue formation.

As used herein, the term "dextran" refers to a complex, branched polysaccharide made of glucose molecules joined into chains of varying lengths. A form of dextran known as native dextran has been shown by several investigators to be enzymatically produced by enzymes liberated by *L. mesenteroides* acting on sucrose and also to be produced by another bacteria, *Leuconostoc* sp. The production of native dextran is summarized in Bixler et al., *Industrial and Engineering Chemistry*, pages 692-705, April 1953, which is incorporated by reference in its entirety.

The term "dextran derivative" refers to any of the family of dextran polymers that have acetate, propionate, and/or succinate groups attached via ester linkages to a significant fraction of the dextran polymer's hydroxyl groups. In one embodiment, the dextran polymer derivative is selected from the group consisting of dextran acetate, dextran propionate, dextran succinate, dextran acetate propionate, dextran acetate succinate, dextran propionate succinate, dextran acetate propionate succinate, and mixtures thereof. In another embodiment, the dextran polymer derivative is dextran acetate succinate. In yet another embodiment, the dextran polymer derivative is dextran propionate succinate.

One embodiment of the disclosure relates to a composition comprising, consisting essentially of, or yet further consisting of a polysaccharide which comprises, consists essentially of, or yet further consists of a first repeat unit and a second repeat unit, wherein the first repeat unit has formula (I):

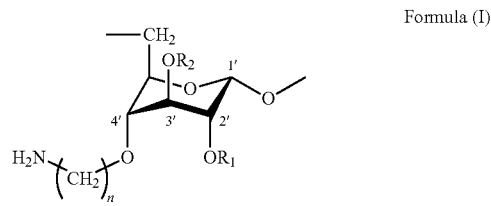

Formula (I)

wherein the second repeat unit has formula (II):

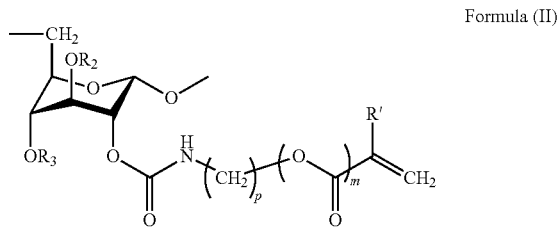

Formula (II)

wherein R1 is selected from a group consisting of hydrogen, —OCONH(CH$_2$)$_p$(COO)$_m$CR'=CH$_2$, and —O(CH$_2$)$_n$NH$_2$, wherein R' is hydrogen or a methyl group, n is no less than 1, m is no less than 1, and p is no less than 1; wherein R2 is selected from a group consisting of hydrogen, —OCONH(CH$_2$)$_p$(COO)$_m$CR'=CH$_2$, and —O(CH$_2$)$_n$NH$_2$, wherein R' is hydrogen or a methyl group, n is no less than 1, m is no less than 1, and p is no less than 1; wherein R3 is selected from a group consisting of hydrogen, —OCONH(CH$_2$)$_p$(COO)$_m$CR'=CH$_2$, and —O(CH$_2$)$_n$NH$_2$, wherein R' is hydrogen or a methyl group, n is no less than 1, m is no less than 1, and p is no less than 1. In one embodiment, the polysaccharide has formula (III):

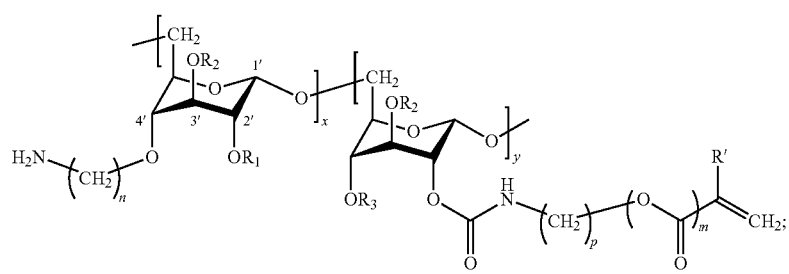

Formula (III)

wherein x is more than 1 and y is more than 1. In some embodiments, p=2. In some embodiments, m=1. In one embodiment, R' is a methyl group. In one embodiment, n=2 or 3. In another embodiment, —O(CH$_2$)$_n$NH$_2$ is formula (IV):

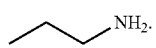

Formula (IV)

In another embodiment, —O(CH$_2$)$_n$NH$_2$ has formula (V):

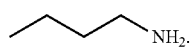

Formula (V)

In one embodiment, —OCONH(CH$_2$)$_p$(COO)$_m$CR'=CH$_2$ has formula (VI):

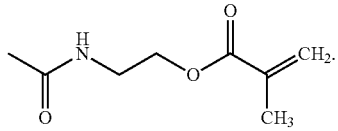

Formula (VI)

In some embodiment, R1 is formula IV, R2 is hydrogen or formula VI, and R3 is hydrogen or formula VI; wherein R1 is hydrogen or formula VI, R2 is formula IV, and R3 is hydrogen or formula VI; wherein R1 is hydrogen or formula VI, R2 is hydrogen or formula VI, and R3 is formula IV; wherein R1 is formula IV, R2 is formula IV or formula VI, and R3 is formula IV or formula VI, or wherein R1 is formula VI, R2 is formula IV, and R3 is formula IV. In some embodiments, R1 has formula V, R2 is hydrogen or formula VI, and R3 is hydrogen or formula VI; wherein R1 is hydrogen or formula VI, R2 is formula V, and R3 is hydrogen or formula VI; wherein R1 is hydrogen or formula VI, R2 is hydrogen or formula VI, and R3 is formula V; wherein R1 is formula V, R2 is formula V or formula VI, and R3 is formula V or formula VI; or wherein R1 is formula VI, R2 is formula V, and R3 is formula V.

In one aspect, the polysaccharide comprises, consists essentially of, or yet further consists of dextran. In some embodiments, the dextran has an average molecular weight ranging from at least 2,000 to 2,000,000 Da. In a different embodiment, the dextran has an average molecular weight of 200,000 Da. In one embodiment, the dextran has more than 13 repeat units. In another embodiment, the dextran has 10, 100, 500, $10^4$, or more than $10^4$ repeat units. A non-exclusive list of dextran derivatives is provided in Table 1. In some embodiments, the repeat unit comprises, consists essentially of, or yet further consists of an amine group. In a further embodiment, the polysaccharide comprises, consists essentially of, or yet further consists of at least one hydrolytically degradable moiety, wherein the hydrolytically degradable moiety is disposed between the biocompatible glucose repeat unit and a crosslinking group. In one embodiment, the crosslinking group comprises, consists essentially of, or yet further consists of an unsaturated vinyl group. In another embodiment, the hydrolytically degradable moiety comprises, consists essentially of, or yet further consists of an ester group. In some embodiment, the amine group comprises, consists essentially of, or yet further consists of a primary amine group. In one embodiment, the amine group and the crosslinking group may be on the same or different repeat units. In some embodiments, the polysaccharide is crosslinked. In a different embodiment, the composition is a hydrogel. In one embodiment, the composition further comprises, consists essentially of, or yet further consists of a bioactive agent.

TABLE 1

| | R$_1$ | R$_2$ | R$_3$ |
|---|---|---|---|
| Dex | H | H | H |
| DexEA | ~~~NH$_2$ | H | H |
| DexEA | H | ~~~NH$_2$ | H |
| DexEA | H | H | ~~~NH$_2$ |
| DexEA | ~~~NH$_2$ | ~~~NH$_2$ | H |
| DexEA | ~~~NH$_2$ | H | ~~~NH$_2$ |
| DexEA | H | ~~~NH$_2$ | ~~~NH$_2$ |
| DexEA | ~~~NH$_2$ | ~~~NH$_2$ | ~~~NH$_2$ |
| DexPA | ~~~~NH$_2$ | H | H |
| DexPA | H | ~~~~NH$_2$ | H |
| DexPA | H | H | ~~~~NH$_2$ |

TABLE 1-continued

| | R₁ | R₂ | R₃ |
|---|---|---|---|
| DexPA | propylamine | propylamine | H |
| DexPA | propylamine | H | propylamine |
| DexPA | H | propylamine | propylamine |
| DexPA | propylamine | propylamine | propylamine |
| DexIEA | N-acetylaminoethyl acrylate | H | H |
| DexIEA | H | N-acetylaminoethyl acrylate | H |
| DexIEA | H | H | N-acetylaminoethyl acrylate |
| DexIEA | N-acetylaminoethyl acrylate | N-acetylaminoethyl acrylate | H |
| DexIEA | N-acetylaminoethyl acrylate | H | N-acetylaminoethyl acrylate |
| DexIEA | H | N-acetylaminoethyl acrylate | N-acetylaminoethyl acrylate |
| DexIEA | N-acetylaminoethyl acrylate | N-acetylaminoethyl acrylate | N-acetylaminoethyl acrylate |
| DexIEAE | propylamine | N-acetylaminoethyl acrylate | H |
| DexIEAE | propylamine | H | N-acetylaminoethyl acrylate |

TABLE 1-continued

|  | R₁ | R₂ | R₃ |
| --- | --- | --- | --- |
| DexIEAE | propylamine (CH₂CH₂NH₂) | acetamidoethyl acrylate | acetamidoethyl acrylate |
| DexIEAE | acetamidoethyl acrylate | propylamine | H |
| DexIEAE | H | propylamine | acetamidoethyl acrylate |
| DexIEAE | acetamidoethyl acrylate | propylamine | acetamidoethyl acrylate |
| DexIEAE | acetamidoethyl acrylate | H | propylamine |
| DexIEAE | H | acetamidoethyl acrylate | propylamine |
| DexIEAE | acetamidoethyl acrylate | acetamidoethyl acrylate | propylamine |
| DexIEAE | propylamine | propylamine | acetamidoethyl acrylate |
| DexIEAE | propylamine | acetamidoethyl acrylate | propylamine |
| DexIEAE | acetamidoethyl acrylate | propylamine | propylamine |
| DexIEAP | butylamine (CH₂CH₂CH₂NH₂) | acetamidoethyl acrylate | H |

TABLE 1-continued

| | R₁ | R₂ | R₃ |
|---|---|---|---|
| DexIEAP | butylamine | H | AEA |
| DexIEAP | butylamine | AEA | AEA |
| DexIEAP | AEA | butylamine | H |
| DexIEAP | H | butylamine | AEA |
| DexIEAP | AEA | butylamine | AEA |
| DexIEAP | H | AEA | butylamine |
| DexIEAP | AEA | H | butylamine |
| DexIEAP | AEA | AEA | butylamine |
| DexIEAP | butylamine | butylamine | AEA |
| DexIEAP | butylamine | AEA | butylamine |
| DexIEAP | AEA | butylamine | butylamine |

(where "butylamine" = CH₃CH₂CH₂CH₂NH₂ group, and "AEA" = N-acetyl-2-aminoethyl acrylate group: CH₃C(O)NH-CH₂CH₂-O-C(O)-CH=CH₂)

TABLE 1-continued

| | R₁ | R₂ | R₃ |
|---|---|---|---|
| DexIEM | CH₃C(O)NH-CH₂CH₂-O-C(O)-C(=CH₂)-CH₃ | H | H |
| DexIEM | H | CH₃C(O)NH-CH₂CH₂-O-C(O)-C(=CH₂)-CH₃ | H |
| DexIEM | H | H | CH₃C(O)NH-CH₂CH₂-O-C(O)-C(=CH₂)-CH₃ |
| DexIEM | CH₃C(O)NH-CH₂CH₂-O-C(O)-C(=CH₂)-CH₃ | CH₃C(O)NH-CH₂CH₂-O-C(O)-C(=CH₂)-CH₃ | H |
| DexIEM | CH₃C(O)NH-CH₂CH₂-O-C(O)-C(=CH₂)-CH₃ | H | CH₃C(O)NH-CH₂CH₂-O-C(O)-C(=CH₂)-CH₃ |
| DexIEM | H | CH₃C(O)NH-CH₂CH₂-O-C(O)-C(=CH₂)-CH₃ | CH₃C(O)NH-CH₂CH₂-O-C(O)-C(=CH₂)-CH₃ |
| DexIEM | CH₃C(O)NH-CH₂CH₂-O-C(O)-C(=CH₂)-CH₃ | CH₃C(O)NH-CH₂CH₂-O-C(O)-C(=CH₂)-CH₃ | CH₃C(O)NH-CH₂CH₂-O-C(O)-C(=CH₂)-CH₃ |
| DexIEME | CH₃CH₂CH₂-NH₂ | CH₃C(O)NH-CH₂CH₂-O-C(O)-C(=CH₂)-CH₃ | H |
| DexIEME | CH₃CH₂CH₂-NH₂ | H | CH₃C(O)NH-CH₂CH₂-O-C(O)-C(=CH₂)-CH₃ |
| DexIEME | CH₃CH₂CH₂-NH₂ | CH₃C(O)NH-CH₂CH₂-O-C(O)-C(=CH₂)-CH₃ | CH₃C(O)NH-CH₂CH₂-O-C(O)-C(=CH₂)-CH₃ |
| DexIEME | CH₃C(O)NH-CH₂CH₂-O-C(O)-C(=CH₂)-CH₃ | CH₃CH₂CH₂-NH₂ | H |

TABLE 1-continued

| | R₁ | R₂ | R₃ |
|---|---|---|---|
| DexIEME | H | CH₂CH₂CH₂-NH₂ | CH₃-C(=O)-NH-CH₂CH₂-O-C(=O)-C(CH₃)=CH₂ |
| DexIEME | CH₃-C(=O)-NH-CH₂CH₂-O-C(=O)-C(CH₃)=CH₂ | CH₂CH₂CH₂-NH₂ | CH₃-C(=O)-NH-CH₂CH₂-O-C(=O)-C(CH₃)=CH₂ |
| DexIEME | H | CH₃-C(=O)-NH-CH₂CH₂-O-C(=O)-C(CH₃)=CH₂ | CH₂CH₂CH₂-NH₂ |
| DexIEME | CH₃-C(=O)-NH-CH₂CH₂-O-C(=O)-C(CH₃)=CH₂ | H | CH₂CH₂CH₂-NH₂ |
| DexIEME | CH₃-C(=O)-NH-CH₂CH₂-O-C(=O)-C(CH₃)=CH₂ | CH₃-C(=O)-NH-CH₂CH₂-O-C(=O)-C(CH₃)=CH₂ | CH₂CH₂CH₂-NH₂ |
| DexIEME | CH₂CH₂CH₂-NH₂ | CH₂CH₂CH₂-NH₂ | CH₃-C(=O)-NH-CH₂CH₂-O-C(=O)-C(CH₃)=CH₂ |
| DexIEME | CH₂CH₂CH₂-NH₂ | CH₃-C(=O)-NH-CH₂CH₂-O-C(=O)-C(CH₃)=CH₂ | CH₂CH₂CH₂-NH₂ |
| DexIEME | CH₃-C(=O)-NH-CH₂CH₂-O-C(=O)-C(CH₃)=CH₂ | CH₂CH₂CH₂-NH₂ | CH₂CH₂CH₂-NH₂ |
| DexIEMP | CH₂CH₂CH₂CH₂-NH₂ | CH₃-C(=O)-NH-CH₂CH₂-O-C(=O)-C(CH₃)=CH₂ | H |
| DexIEMP | CH₂CH₂CH₂CH₂-NH₂ | H | CH₃-C(=O)-NH-CH₂CH₂-O-C(=O)-C(CH₃)=CH₂ |

TABLE 1-continued

| | R₁ | R₂ | R₃ |
|---|---|---|---|
| DexIEMP | propylamine (–CH₂CH₂CH₂NH₂) | acetamidoethyl methacrylate (CH₃C(O)NH–CH₂CH₂–O–C(O)–C(CH₃)=CH₂) | acetamidoethyl methacrylate (CH₃C(O)NH–CH₂CH₂–O–C(O)–C(CH₃)=CH₂) |
| DexIEMP | acetamidoethyl methacrylate | propylamine | H |
| DexIEMP | H | propylamine | acetamidoethyl methacrylate |
| DexIEMP | acetamidoethyl methacrylate | propylamine | acetamidoethyl methacrylate |
| DexIEMP | acetamidoethyl methacrylate | H | propylamine |
| DexIEMP | H | acetamidoethyl methacrylate | propylamine |
| DexIEMP | acetamidoethyl methacrylate | acetamidoethyl methacrylate | propylamine |
| DexIEMP | propylamine | propylamine | acetamidoethyl methacrylate |
| DexIEMP | propylamine | acetamidoethyl methacrylate | propylamine |
| DexIEMP | acetamidoethyl methacrylate | propylamine | propylamine |

Examples of bioactive agents for use in the dissolvable hydrogel and/or compositions described herein include, without limitations, medicaments; vitamins; mineral supplements; substances used for the treatment, prevention, diagnosis, cure, or mitigation of disease or illness; or substances which attest the structure or function of the body; or pro-drugs, which become biologically active or more active after they have been placed in a predetermined physiological environment. In some embodiments, bioactive agent(s) include, but are not limited to, growth factors, such as members of the transforming growth factor (TGF) gene family (e.g., TGF-β1, TGF-β2, and TGF-β3), fibroblast growth factors (FGFs), platelet derived growth factors (PDGFs), epidermal growth factors (EGFs), connective tissue activated peptides (CTAPs), osteogenic factors, bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB), vascular endothelium growth factor (VEGF); hormones, e.g., but not limited to, insulin, glucagon, and estrogen; therapeutic agents or drugs, e.g., but not limited to wound-healing agents, anti-inflammatory steroids, and chemotherapeutics; antimicrobial agents; an anesthetic; and biologically active analogs, fragments, and derivatives of such growth factors; and any combinations thereof.

In some embodiments, the bioactive agent(s) can be pharmaceutically active agent(s). Non-limiting examples of the pharmaceutically active agent(s) can include (1) non-steroidal anti-inflammatory drugs (NSAIDs) analgesics, including, but not limited to, diclofenac, ibuprofen, ketoprofen, and naproxen; (2) opiate agonist analgesics, including, but not limited to, codeine, vancomycin, ceftazidime, fentanyl, hydromorphone, and morphine; (3) salicylate analgesics, including, but not limited to, aspirin (ASA) (or enteric coated ASA); (4) H1-blocker antihistamines, including, but not limited to, clemastine and terfenadine; (5) H2-blocker antihistamines, including, but not limited to, cimetidine, famotidine, nizatidine, and ranitidine; (6) anti-infective agents, including, but not limited to, mupirocin; (7) antianaerobic anti-infectives, including, but not limited to, chloramphenicol metronidazole and clindamycin; (8) antifungal antibiotic anti-infectives, including, but not limited to, amphotericin B, clotrimazole, fluconazole, and ketoconazole; (9) macrolide antibiotic anti-infectives, including, but not limited to, azithromycin and erythromycin; (10) miscellaneous beta-lactam antibiotic anti-infectives, including, but not limited to, aztreonam and imipenem; (11) penicillin antibiotic anti-infectives, including, but not limited to, nafcillin, oxacillin, penicillin G, and penicillin V; (12) quinolone antibiotic anti-infectives, including, but not limited to, ciprofloxacin and norfloxacin; (13) tetracycline antibiotic anti-infectives, including, but not limited to, doxycycline, minocycline, and tetracycline; (14) antituberculosis antimycobacterial anti-infectives including, but not limited to, isoniazid (INH), and rifampin; (15) antiprotozoal anti-infectives, including, but not limited to, atovaquone and dapsone; (16) antimalarial antiprotozoal anti-infectives, including, but not limited to, chloroquine and pyrimethamine; (17) antiretroviral anti-infectives, including, but not limited to, ritonavir and zidovudine; (18) antiviral anti-infective agents, including, but not limited to, acyclovir, ganciclovir, interferon alpha, and rimantadine; (19) alkylating antineoplastic agents, including, but not limited to, carboplatin and cisplatin; (20) nitrosourea alkylating antineoplastic agents, including, but not limited to, carmustine (BCNU); (21) antimetabolite antineoplastic agents, including, but not limited to, methotrexate; (22) pyrimidine analog antimetabolite antineoplastic agents, including, but not limited to, fluorouracil (5-FU), gemcitabine, orceftazidime, aminoglycodi meroperium, or ticarcillin and tobramycin; (23) hormonal antineoplastics, including, but not limited to, goserelin, leuprolide, and tamoxifen; (24) natural antineoplastics, including, but not limited to, aldesleukin, interleukin-2, docetaxel, etoposide (VP-16), interferon alpha, paclitaxel, and tretinoin (ATRA); (25) antibiotic natural antineoplastics, including, but not limited to, bleomycin, actinomycin, daunorubicin, doxorubicin, and mitomycin; (26) vinca alkaloid natural antineoplastics, including, but not limited to, vinblastine and vincristine; (27) autonomic agents, including, but not limited to, nicotine; (28) anticholinergic autonomic agents, including, but not limited to, benztropine and trihexyphenidyl; (29) antimuscarinic anticholinergic autonomic agents, including, but not limited to, atropine and oxybutynin; (30) ergot alkaloid autonomic agents, including, but not limited to, bromocriptine; (31) cholinergic agonist parasympathomimetics, including, but not limited to, pilocarpine; (32) cholinesterase inhibitor parasympathomimetics, including, but not limited to, pyridostigmine; (33) alpha-blocker sympatholytics, including, but not limited to, prazosin; (34) beta-blocker sympatholytics, including, but not limited to atenolol; (35) adrenergic agonist sympathomimetics, including, but not limited to, albuterol and dobutamine; (36) cardiovascular agents, including, but not limited to, aspirin (ASA), plavix (Clopidogrel bisulfate) etc.; (37) beta-blocker antianginals, including, but not limited to, atenolol and propranolol; (38) calcium-channel blocker antianginals, including, but not limited to, nifedipine and verapamil; (39) nitrate antianginals, including, but not limited to, isosorbide dinitrate (ISDN); (40) cardiac glycoside antiarrhythmics, including, but not limited to, digoxin; (41) class I antiarrhythmics, including, but not limited to, lidocaine, mexiletine, phenytoin, procainamide, and quinidine; (42) class II antiarrhythmics, including, but not limited to, atenolol, metoprolol, propranolol, and timolol; (43) class III antiarrhythmics, including, but not limited to, amiodarone; (44) class TV antiarrhythmics, including, but not limited to, diltiazem and verapamil; (45) alpha-blocker antihypertensives, including, but not limited to, prazosin; (46) angiotensin-converting enzyme inhibitor (ACE inhibitor) antihypertensives, including, but not limited to, captopril and enalapril; (47) beta blocker antihypertensives, including, but not limited to, atenolol, metoprolol, nadolol, and propranolol; (48) calcium-channel blocker antihypertensive agents, including, but not limited to, diltiazem and nifedipine; (49) central-acting adrenergic antihypertensives, including, but not limited to, clonidine and methyldopa; (50) diuretic antihypertensive agents, including, but not limited to, amiloride, furosemide, hydrochlorothiazide (HCTZ), and spironolactone; (51) peripheral vasodilator antihypertensives, including, but not limited to, hydralazine and minoxidil; (52) antilipemics, including, but not limited to, gemfibrozil and probucol; (53) bile acid sequestrant antilipemics, including, but not limited to, cholestyramine; (54) HMG-CoA reductase inhibitor antilipemics, including, but not limited to, lovastatin and pravastatin; (55) inotropes, including, but not limited to, amrinone, dobutamine, and dopamine; (56) cardiac glycoside inotropes, including, but not limited to, digoxin; (57) thrombolytic agents or enzymes, including, but not limited to, alteplase (TPA), anistreplase, streptokinase, and urokinase; (58) dermatological agents, including, but not limited to, colchicine, isotretinoin, methotrexate, minoxidil, tretinoin (ATRA); (59) dermatological corticosteroid anti-inflammatory agents, including, but not limited to, betamethasone and dexamethasone; (60) antifungal topical anti-infectives, including, but not limited to, amphotericin B, clotrimazole, miconazole, and nystatin; (61) antiviral topical anti-infectives, including, but not limited to, acyclovir; (62) topical antineoplastics, including, but not limited to, fluorouracil (5-FU); (63) electrolytic and renal agents, including, but not limited to, lactulose; (64) loop diuretics, including, but not limited to, furosemide; (65) potassium-sparing diuretics, including, but not limited to, triamterene; (66) thiazide diuretics, including, but not limited to, hydrochlorothiazide (HCTZ); (67) uricosuric agents, including, but not limited to, probenecid; (68) enzymes including, but not limited to, RNase and DNase; (69) immunosuppressive agents, including, but not limited to, cyclosporine, steroids, methotrexate, tacrolimus, sirolimus, rapamycin; (70) antiemetics, including, but not limited to, prochlorperazine; (71) salicylate gastrointestinal anti-inflammatory agents, including, but not limited to, sulfasalazine; (72) gastric acid-pump inhibitor anti-ulcer agents, including, but not limited to, omeprazole; (73) H2-blocker anti-ulcer agents, including, but not limited to, cimetidine, famotidine, nizatidine, and ranitidine; (74) digestants, including, but not limited to, pancrelipase; (75) prokinetic agents, including, but not limited to, erythromycin; (76) opiate agonist intravenous anesthetics, including, but not limited to, fentanyl; (77) hematopoietic antianemia agents, including, but not limited to, erythropoietin, filgrastim (G-CSF), and sargramostim (GM-CSF); (78) coagulation agents, including, but not limited to, antihemophilic factors 1-10 (AHF 1-10); (79) anticoagulants, including, but not limited to, warfarin, heparin (important for heparin bound polymers and cardiopulmonary bypass pump circuits), argatroban—each works by a different mechanism and is metabolized differently; (80) growth receptor inhibitors, including, but not limited to, erlotinib and gefitinib; (82) abortifacients, including, but not limited to, methotrexate; (83) antidiabetic agents, including, but not limited to, insulin; (84) oral contraceptives, including, but not limited to, estrogen and progestin; (85) progestin contraceptives, including, but not limited to, levonorgestrel and norgestrel; (86) estrogens including, but not limited to, conjugated estrogens, diethylstilbestrol (DES), estrogen (estradiol, estrone, and estropipate); (87) fertility agents, including, but not limited to, clomiphene, human chorionic gonadotropin (HCG), and menotropins; (88) parathyroid agents including, but not limited to, calcitonin; (89) pituitary hormones, including, but not limited to, desmopressin, goserelin, oxytocin, and vasopressin (ADH); (90) progestins, including, but not limited to, medroxyprogesterone, norethindrone, and progesterone; (91) thyroid hormones, including, but not limited to, levothyroxine; (92) immunobiological agents, including, but not limited to, interferon beta-1b and interferon gamma-1b; (93) immunoglobulins, including, but not limited to, immune globulin IM, IMIG, IGIM and immune globulin IV, IVIG, IGIV; (94) amide local anesthetics, including, but not limited to, lidocaine; (95) ester local anesthetics, including, but not limited to, benzocaine and procaine; (96) musculoskeletal corticosteroid anti-inflammatory agents, including, but not limited to, beclomethasone, betamethasone, cortisone, dexamethasone, hydrocortisone, and prednisone; (97) musculoskeletal anti-inflammatory immunosuppressives, including, but not limited to, azathioprine, cyclophosphamide, and methotrexate; (98) musculoskeletal nonsteroidal anti-inflammatory drugs (NSAIDs), including, but not limited to, diclofenac, ibuprofen, ketoprofen, ketorolac, and naproxen; (99) skeletal muscle relaxants, including, but not limited to, baclofen, cyclobenzaprine, and diazepam; (100) reverse neuromuscular blocker skeletal muscle relaxants, including, but not limited to, pyridostigmine; (101) neurological agents, including, but not limited to, nimodipine, riluzole, tacrine and ticlopidine; (102) anticonvulsants, including, but not limited to, carbamazepine, gabapentin, lamotrigine, phenytoin, and valproic acid; (103) barbiturate anticonvulsants, including, but not limited to, phenobarbital and primidone; (104) benzodiazepine anticonvulsants, including, but not limited to, clonazepam, diazepam, and lorazepam; (105) anti-parkinsonian agents, including, but not limited to, bromocriptine, levodopa, carbidopa, and pergolide; (106) anti-vertigo agents, including, but not limited to, meclizine; (107) opiate agonists, including, but not limited to, codeine, fentanyl, hydromorphone, methadone, and morphine; (108) opiate antagonists, including, but not limited to, naloxone; (109) beta-blocker anti-glaucoma agents, including, but not limited to, timolol; (110) miotic anti-glaucoma agents, including, but not limited to, pilocarpine; (111) ophthalmic aminoglycoside anti-infectives, including, but not limited to, gentamicin, neomycin, and tobramycin; (112) ophthalmic quinolone anti-infectives, including, but not limited to, ciprofloxacin, norfloxacin, and ofloxacin; (113) ophthalmic corticosteroid anti-inflammatory agents, including, but not limited to, dexamethasone and prednisolone; (114) ophthalmic nonsteroidal anti-inflammatory drugs (NSAIDs), including, but not limited to, diclofenac; (115) antipsychotics, including, but not limited to, clozapine, haloperidol, and risperidone; (116) benzodiazepine anxiolytics, sedatives and hypnotics, including, but not limited to, clonazepam, diazepam, lorazepam, oxazepam, and prazepam; (117) psychostimulants, including, but not limited to, methylphenidate and pemoline; (118) antitussives, including, but not limited to, codeine; (119) bronchodilators, including, but not limited to, theophylline; (120) adrenergic agonist bronchodilators, including, but not limited to, albuterol; (121) respiratory corticosteroid anti-inflammatory agents, including, but not limited to, dexamethasone; (122) antidotes, including, but not limited to, flumazenil and naloxone; (123) heavy metal antagonists/chelating agents, including, but not limited to, penicillamine; (124) deterrent substance abuse agents, including, but not limited to, disulfiram, naltrexone, and nicotine; (125) withdrawal substance abuse agents, including, but not limited to, bromocriptine; (126) minerals, including, but not limited to, iron, calcium, and magnesium; (127) vitamin B compounds, including, but not limited to, cyanocobalamin (vitamin B12) and niacin (vitamin B3); (128) vitamin C compounds, including, but not limited to, ascorbic acid; (129) vitamin D compounds, including, but not limited to, calcitriol; (130) antiparasitic compounds including, but not limited to, metronidazole; (131) bronchodilators, including but not limited to salmeterol, and beta agonists; (132) leukotriene blockers/modifiers, including montelukast or zileuton; (133) inhaled steroids including, but not limited to, fluticasone, beclomethasone, or budesonide. Anti-bleeding (hemostatic) agents, including, but not limited to, protamine and anthelmintics, radiation sensitizers, and other drugs, including, but not limited to, ricin and cyclosporine are also included. Additional anticancer drugs, including, but not limited to, pycnidione as well as anti-Myc inhibitors. Hydrogel can comprise, consist essentially of, or yet further consist of silver or silver salts for antibacterial activity.

Thus, in a further embodiment, the bioactive agent is selected from a group consisting of pharmaceutical agents, drugs, cells, gases and gaseous precursors, synthetic organic molecules, proteins, enzymes, growth factors, vitamins, steroid, polyanions, nucleosides, nucleotides, polynucleotides, nanoparticles, diagnostic agents, genetic materials, and any combinations thereof. In some embodiments, the growth factor is selected from a group consisting of epidermal growth factor, platelet derived growth factor, hepatocytic growth factor, human growth hormone, fibroblast growth factor, vascular endothelium growth factor and combinations thereof.

In another aspect, the disclosure relates to methods of forming the composition into a hydrogel, comprising, consisting essentially of, or yet further consisting of combining in a solution the composition of any one of claims 1-28 for a sufficient period of time; and exposing the solution to UV light, wherein a crosslinked polymer network structure is formed within the composition after exposure. In one embodiment, the method further comprises, consists essentially of, or yet further consists of allowing the hydrogel composition to dry. In another embodiment, the hydrogel is allowed to dry for a period of time prior to the completion of the crosslinking reaction. In some embodiments, the method further comprises, consists essentially of, or yet further consists of fragmenting the hydrogel composition. In a different embodiment, the hydrogel is fragmented after drying. In one embodiment, the method further comprises, consists essentially of, or yet further consists of casting the hydrogel composition into a predetermined cast shape. In another embodiment, the method also comprises, consists essentially of, or yet further consists of cutting, folding, stretching, coring, and/or machining the composition to a predetermined shape or dimension that is different from the cast shape. In one embodiment, the method comprises, consists essentially of, or yet further consists of incorporating the bioactive agent into the composition, wherein the bioactive agent comprises, consists essentially of, or yet further consists of a medicament; vitamin, a mineral supplement, a pro-drug, a growth factor, or a pharmaceutically active agent.

In one aspect, the disclosure relates to methods of synthesizing a macromer, comprising consisting essentially of, or yet further consisting of reacting a first compound comprising consisting essentially of, or yet further consisting of —$(CH_2)_p(COO)_mCR'=CH_2$ with a hydroxyl group of a polysaccharide to give rise to a first macromer comprising consisting essentially of, or yet further consisting of a polymerizing moiety and a hydrolytically degradable linker, where the macromer is formula II, and reacting the first macromer with a second compound comprising consisting essentially of, or yet further consisting of —$(CH_2)_nNH_2$ with a free hydroxyl group of the first macromere to form a second macromere, wherein the second macromer is formula III. In one embodiment, the first and second macromers are biodegradable. In another embodiment, the second macromers are more biocompatible than the first macromers. In some embodiments, the hydroxyl group may react with an isocyanate group to form a urethane group in presence of dibutyltin dilaurate, thus incorporating a biodegradable ester group and an unsaturated vinyl group into the polysaccharide. In a different embodiment, the hydroxyl group is substituted to give rise to a primary amine side group in presence of trimethylamine. In one embodiment, the polysaccharide comprises, consists essentially of, or yet further consists of dextran. In some embodiments, the dextran has an average molecular weight ranging from at least 2000 to 200,000 Da.

In one embodiment, the degree of substituted hydroxyl group of —$OCONH(CH_2)_p(COO)_mCR'=CH_2$ on the polysaccharide is from 0.05 to 0.97. In one embodiment, the degree of substituted hydroxyl group of —$O(CH_2)_nNH_2$ on the polysaccharide is from 0.03 to 0.95.

In a further embodiment, the disclosure relates to a hydrogel forming system, wherein the system comprises, consists essentially of, or yet further consists of a polysaccharide, which comprises, consists essentially of, or yet further consists of the first repeat unit of formula I and the second repeat unit of formula II, wherein at least one repeat unit having at least a polymerizing moiety; wherein the system is polymerized after exposed to UV light, thus forming a three-dimensional polymer network. In one embodiment, the polysaccharide is dextran. In another embodiment, dextran has an average molecular weight ranging from at least 2000 to 200,000 Daltons, and at least 13 to 1234 repeat units. In a different embodiment, the hydrogel-forming system has a weight concentration from 0.01 to 99.99%. In some embodiments, the hydrogel is capable of loading a protein molecule and releasing the molecule in a controlled manner.

In one embodiment, the disclosure also relates to methods of attenuating scarring, which methods comprise, consist essentially of, or yet further consist of excising the scarred skin, and regenerating the skin on scarred skin area with any one of the compositions in the disclosure. In another embodiment, the disclosure relates to methods of promoting cutaneous wound healing or dermal regeneration and skin appendage, which methods comprise, consist essentially of, or yet further consist of applying a portion of injured skin area in any one of the compositions of the disclosure. In one embodiment, the composition is applied topically. In another embodiment, the skin appendage comprises, consists essentially of, or yet further consists of hair follicle, sebaceous glands, and sweat glands. In some embodiments, the injured skin area comprises, consists essentially of, or yet further consists of a scratch, cut, tear, scrape, bruise abrasion, puncture, incision, first-degree burn, second-degree burn, third-degree burn, open wound, skin avulsion, and/or laceration. In one embodiment, the composition is hydrogel. In some embodiment, the hydrogel comprises, consists essentially of, or yet further consists of liquid hydrogel, solid hydrogel, nanosized hydrogel, and/or macrosized hydrogel. In one embodiment, the hydrogel is freeze-dried, cut, minced, or chopped before administration. In some embodiment, the hydrogel can absorb excess fluid, exudate and/or retain moisture.

In some embodiments, the method further comprises, consists essentially of, or yet further consists of placing the composition to an uninjured skin area. In some embodiment, the composition is applied to entire injured area. In one embodiment, the composition comprises, consists essentially of, or yet further consists of a bioactive agent to a subject in need of treatment. In some embodiments, the bioactive agent comprises, consists essentially of, or yet further consists of a medicament, vitamin, a mineral supplement, a pro-drug, a growth factor, or a pharmaceutically active agent. In a further embodiment, said hydrogel is used to regenerate new tissue or protect tissue from being further damaged or deteriorated. In some embodiments, the tissue comprises skin, muscle, bone, liver, lung, skeletal muscle, dental pulp, vasculature, gastrointestinal tract, cardiac tissue, ocular tissue, gut, intervertebral disk, cartilage, ligament, tendon, or the combination thereof.

WORKING EXAMPLES

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to include preferred modes for the practice of the invention. It will be appreciated by those of skill in the art that, in light of the present disclosure, numerous modifications and changes can be made in the particular embodiments exemplified without departing from the intended scope of the invention.

Figure 6:
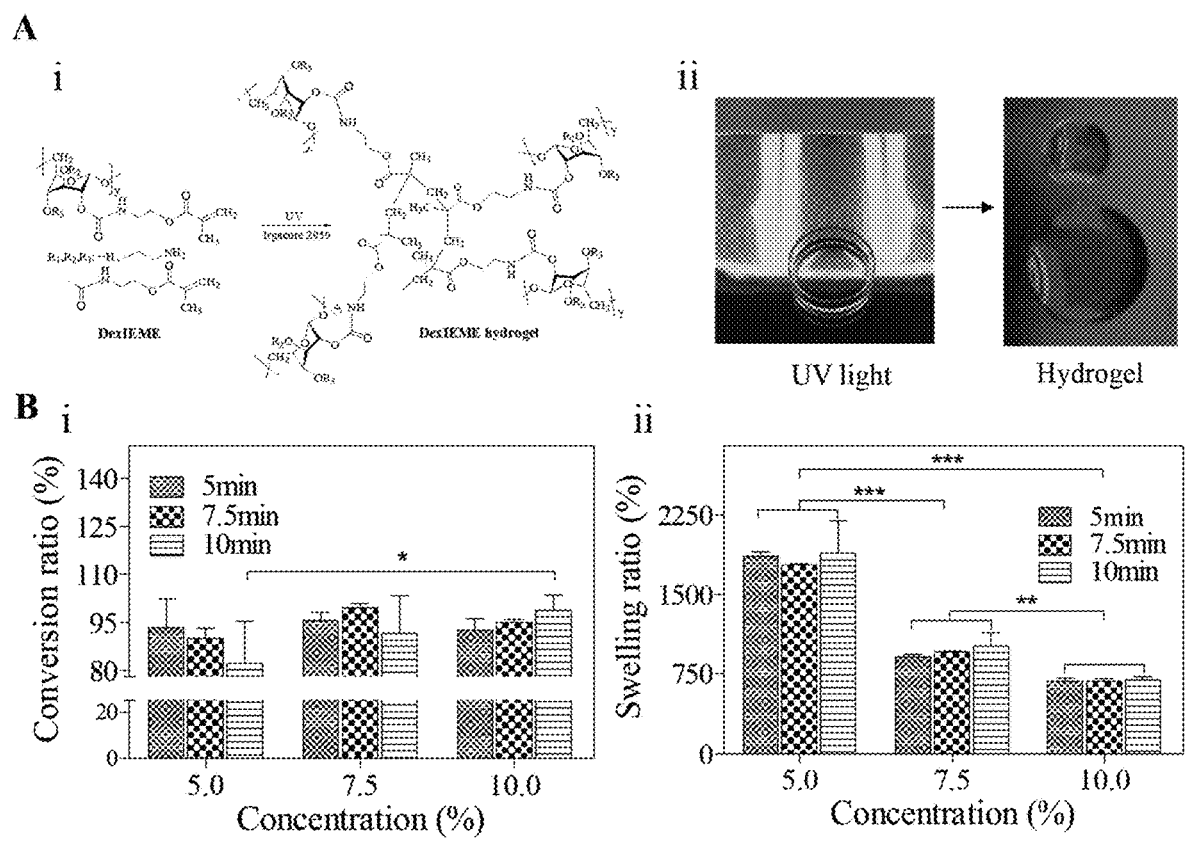
FIG. 6 shows hydrogel preparation.

Hydrogels can be crosslinked by direct chemical reaction, or the reactions can be initiated by chemical initiators or photo-initiators. Photo-initiated crosslinking can offer such advantages as easier control over degree of crosslinking by having direct control over exposure to UV light. For this reason, certain embodiments include hydrogels and hydrogel forming compositions that form hydrogels in a particular period of time. For instance, the compositions may form hydrogels in less than about 1 minute, less than about 5 minutes, less than about 10 minutes, or less than about 20 minutes while exposing to 36 W ultraviolet lamp at 365 nm, thus initiating radical polymerization to form any shaped hydrogels. DexIEME hydrogel structures are shown in FIG. 6A. To optimize the hydrogel crosslinking, FIG. 6B further shows the conversion efficiency and swelling ratios of different conditions, thus narrowing down the ideal crosslinking condition for skin regeneration.

The hydrogel may be kept in place with a dressing. The dressing may protect the wound from bacterial infection, control evaporative water loss and prevent dehydration, control the permeability of oxygen and carbon dioxide, and absorb wound exudates.

In some embodiments, the hydrogel comprises, consists essentially of, or yet further consists of some agents, such as growth factors, cytokines, genes, stem cells, etc., to promote wound repair and complete skin regeneration. In some embodiments, the pharmaceutical agent may be an antibiotic or growth factors. When the hydrogel includes an antibiotic, the antibiotic may be, for example, an antibacterial, antifungal, antiviral, or antimicrobial agent to prevent or reduce infection of the wound.

From the foregoing description, it will be apparent that variations and modifications may be made to the invention described herein to adopt it to various usages and conditions. Such embodiments are also within the scope of the following claims.

Terms listed in single tense also include multiple unless the context indicates otherwise.

Methods for preparing, characterizing, and using the compounds of this invention are illustrated in the following examples. Starting materials are made according to procedures known in the art or as illustrated herein. The following examples are provided so that the invention might be more fully understood. These examples are illustrative only and should not be construed as limiting the invention in any way.

The following non-limiting examples are to further illustrate the disclosure of this patent.

Statistics

All measurements of dextran derivatives and hydrogel properties were performed on three to eight samples for each data point. Either one- or two-way ANOVA tests were performed where appropriate (GraphPad Prism 4.02, GraphPad Software, San Diego, Calif.). Significance levels were determined using post tests and set at: *$p<0.05$, $p<0.01$, and *$p<0.001$. All graphical data is reported.

Example 1

Synthesis of Bioabsorbable Dex Macromers

Figure 2:
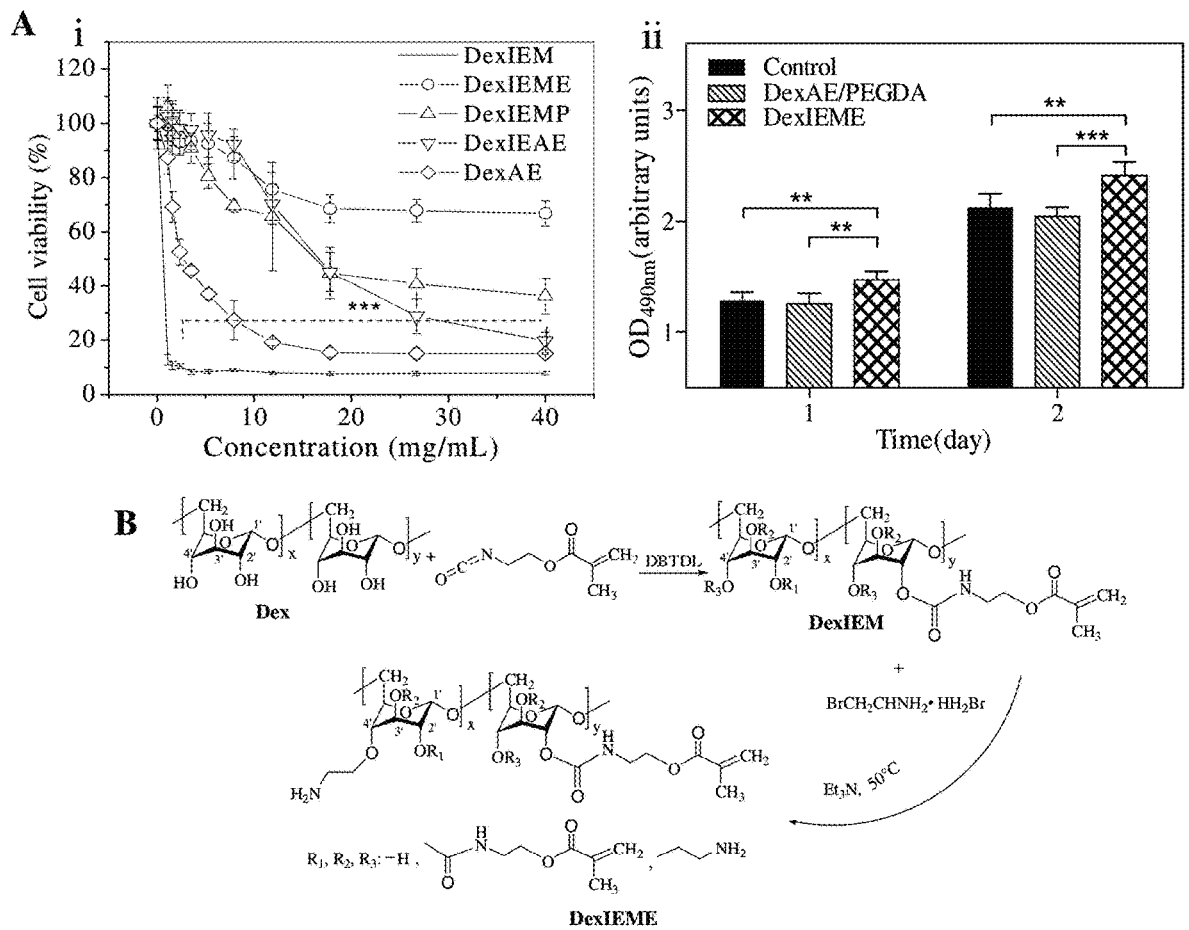
FIG. 2 exemplifies screening biocompatible hydrogel precursors.

The synthesis of dextran macromers involved two steps, as shown in FIG. 2. DexIEM hydrogels were prepared similar to as previously reported (Sun et al. *Carbohydrate Polymers*, Vol. 65, pp. 273-287, 2006). Dextran first reacted with IEM to form dextran-isocyanatoethyl methacrylate (DexIEM) in the presence of DBTDL catalyst. At room temperature (25° C.), dry dextran (MW 40,000; 8.0 g) was dissolved in anhydrous DMSO (70.0 mL) under dry nitrogen gas. DBTDL catalyst (1.2 mL) was injected into the solution at room temperature, and then IM (1.2 mL) was added dropwise. The reaction mixture was stirred at room temperature (25° C.) for 12 hours. The resulting macromer was precipitated in cold excess isopropanol. The product was further purified by dissolution and precipitation in DMSO and isopropanol, respectively. This resulting DexIEM was dried overnight at 37° C. under vacuum.

Biocompatibility is an important consideration for the bioactive scaffolds. The cell viability experiment revealed that DexIEME has superior biocompatibility at higher concentrations (FIG. 2A(i)). DexIEAE is one of the new designs with slightest difference, but DexIEAE also shows significantly greater biocompatibility than Dex-AE. DexIEME has also significantly improved biocompatibility than Dex-AE at lower concentration (Sun et al. *J Biomed Mater Res A*, Vol. 93, pp. 1080-1090, 2010) (FIG. 2A(ii)). The synthesis of DexIEME is illustrated in FIG. 2B. DexIEM was readily obtained by reacting dextran with 2-Isocyanatoethyl methacrylate in the presence of DBTDL catalyst. In this step, a compound with an isocyanate group, a biodegradable ester group and a crosslinkable vinyl group was incorporated into dextran, giving rise to DexIEM. In the second step, as shown in FIG. 2B, DexIEM reacts with BEAHB, thus incorporating amine groups to the free hydroxyl groups of DexIEM to form DexIEME. The reaction occurs in the presence of triethylamine.

After two steps of chemical modification, dextran was turned into a macromer that is both enzymatically and hydrolytically degradable, and with improved biocompatibility. In addition, this modification can incorporate a relatively long chain, and thus no second crosslinker is needed to fabricate hydrogels.

To increase the biocompatibility of the macromer, the primary amine group is incorporated to the DexIEM macromer. The incorporation of amine groups into dextran gives rise to hydrogels with better biocompatible and release properties (Sun et al. Journal of Biomedical Materials Research Part A, Vol. 93A, pp. 1080-1090, 2010). Briefly, dry DexIEM (3.0 g) was dissolved in anhydrous DMSO (30 mL) under dry nitrogen gas. Triethylamine (5.6 mL) was injected into the above solution. And BEAHB (3.75 g) was dissolved in DMSO (10 mL) and then added to the above solution dropwise. This reaction solution was stirred at 50° C. for 8 hours. The reaction mixture was filtered to remove the precipitated $Et_3NH_4Br$. The resulting DexIEME was obtained by precipitating the filtered solution into excess cold isopropyl alcohol. The product was further purified at least three times by dissolution and precipitation with DMSO and cold isopropyl alcohol, respectively. DexIEME was dried at 37° C. under vacuum overnight. The resulting DexIEME was then dialyzed (MWCO: 1000 Da) against distilled water for three days and lyophilized for an additional three days. After the incorporation of amine group, DexIEME shows significantly improved biocompatibility than DexIEM (FIG. 2A(i)).

Chemical Characterization

The dextran and its derived macromers will be characterized for their chemical structure by FTIR and $^1H$ NMR. For FTIR characterization, all samples were dried in a vacuum oven for at least 24 hours and then compressed into pellets with KBr powder (1/10, w/w) for FT-IR characterization (Nicolet Magna 560, Madison, SI). For $^1H$ NMR characterization, samples were dissolved in deuterated DMSO (DMSO-d6) at a concentration of 25% (w/v) and their spectra were recorded on a Varian INOVA 400 MHz spectrometer (Palo Alto, Calif.). The DMSO peak at 2.50 ppm was used as the reference line.

Figure 3:
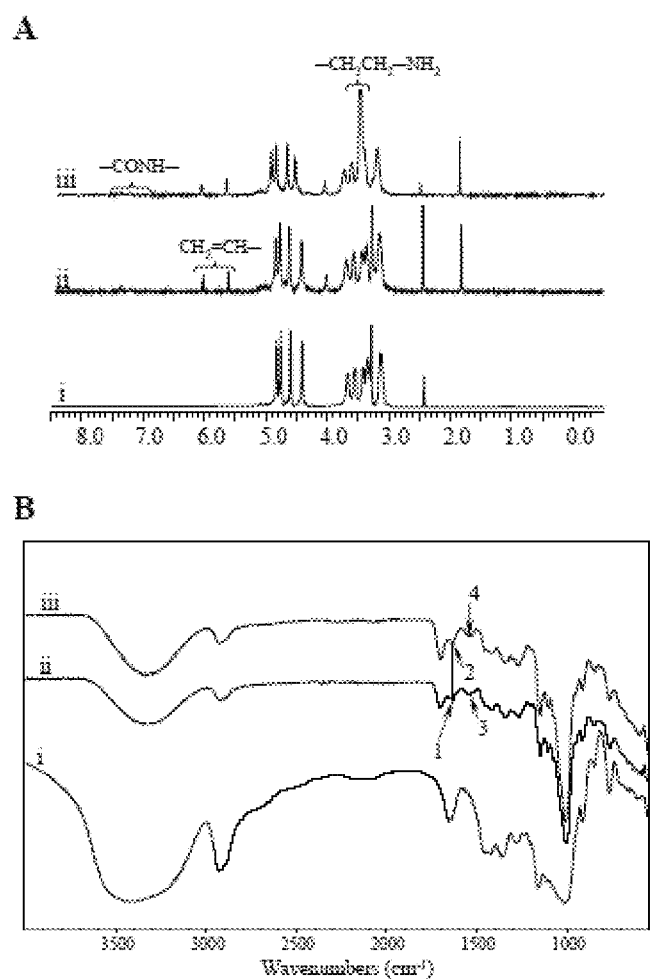
FIG. 3 shows the characterization of DexIEME.

The chemical structures of dextran, DexIEM and DexIEME were further characterized by Nuclear magnetic resonance ($^1H$ NMR) and The Fourier transform infrared (FTIR) and were shown in FIG. 3. As shown in FIG. 3A about the $^1H$ NMR spectra of different macromers, the vinyl end group peaks of DexIEM and DexIEME appeared at 6.16 pm and 5.75 ppm. It is possible that the peaks at 7.33 and 7.47 ppm is assigned to the carbamate (—NH—) proton, and the peak at 3.54 ppm is assigned to the alkyl conjugated with amine group. As shown in FIG. 3B about the FTIR spectra of these macromers, the peaks at 1635 $cm^{-1}$ revealed the typical double-bond stretch vibration, confirming the successful conjugation of vinyl group. The peak at 1541 $cm^{-1}$ in DexIEM is attributed to amide II and shifted to 1535 $cm^{-1}$ in DexIEME due to the N—H stretching vibration of the amine group. Taken together, both NMR and FTIR spectra confirmed the structures of our designed macromers. The characterizations of dextran and its derivatives are shown in FIG. 3.

Example 2

Biocompatibility

To narrow down the hydrogel precursors, the cytotoxicity tests were first performed on dextran derivatives. The biocompatibility was estimated by the proliferation of African green monkey SV40-transformed kidney fibroblast (COS7) cells using MTT assay (Invitrogen). In brief, COS7 cells were seeded in a 96-well plate at a density of 6000 cells per well and incubated in 100 μL DMEM containing 10% FBS for 24 hours. After that, the dextran derivative samples with different concentrations were added to each well. 48 hours later, 20 mL MTT (5 mg/mL in PBS buffer) solution was added to each well and incubated for another 4 hours. Finally, the medium was replaced with 150 mL dimethyl sulfoxide (DMSO). The absorbance was measured at 570 nm by a microplate reader (Bio-Rad, Model 550, USA). The relative cell viability was calculated from the following equations: cell viability (%)=$(OD_{570(samples)})/OD_{570(control)} \times 100\%$, where $OD_{570(samples)}$ is the reading obtained in the presence of samples and $OD_{570(control)}$ is referred to reading in the absence of samples.

Adipose cells are beneficial to both wound healing and hair follicle regeneration (Festa et al. Cell, Vol. 146, pp. 761-771; Schmidt et al. Development, Vol. 140, pp. 1517-1527, 2013). To further examine the biocompatibility of dextran derivatives, the proliferation of human adipose stem cells (ASCs) (Cyagen Biosciences Technology) was detected using the MTS kit (Sigma). ASCs were cultured in DMEM/F-12 containing 10% fetal bovine serum until the cells reached 80% confluence. Briefly, ASCs were cultured in the presence of macromer solution (5.0 μl/ml culture medium) and counted daily or incubated for 4 hours in medium containing 20% (v/v) MTS solution. The medium was then transferred to a 96-well plate, and the results were read in a microplate reader at 490 nm.

Example 3

Macrophage Differentiation

The human monocytic leukaemia THP-1 cell line (American Type Culture Collection) was cultured in RPMI-1640 medium supplemented with 10% FBS and 1% penicillin/streptomycin. According to the published protocols (Freytes et al., *Journal of Cellular Biochemistry*, Vol. 114, pp. 220-229 (2013); Tjiu et al. *J Invest Dermatol*, Vol. 129, pp. 1016-1025 (2008)), THP-1 cells were differentiated into macrophages after 48 hours of treatment with phorbol myristate acetate (50 ng/ml). To test the macromer effect on macrophage proliferation, differentiated macrophage cells ($2.0 \times 10^5$ cells/ml) were incubated in the presence of macromer solution (5.0 μl/ml culture medium) at 37° C. for up to 96 hours under standard humidity and CO2 conditions, and further incubated for 4 hours after adding MTS solution. 120 μl of the medium was transferred to a 96-well plate, and the results were read in a microplate reader at 490 nm.

Polarization of Pro-inflammatory (M1)/Anti-Inflammatory (M2) Macrophages

After THP-1 cells were differentiated into macrophages, they were further polarized into M1 and M2 phonotypes, respectively. M1-polarized macrophage was derived after 48 hours of treatment within RPMI-1640 medium supplemented with 240 ng/ml LPS and 20 ng/ml IFN-γ in and 10% heat-inactivated fetal bovine serum (HI-FBS). M2-polarized macrophage was obtained within the RPMI-1640 medium that contains 20 ng/ml IL-4 and 20 ng/ml IL-13 supplemented with 10% HI-FBS. Similarly, polarized M1/M2 cells ($2.0 \times 10^5$ cells/ml) were incubated in the presence of macromer solution (5.0 μl/ml culture medium) at 37° C. for up to 96 hours, and further incubated for 4 hours after adding MTS solution. 120 μl of the medium was transferred to a 96-well plate, and the results were read in a microplate reader at 490 nm.

Figure 4:
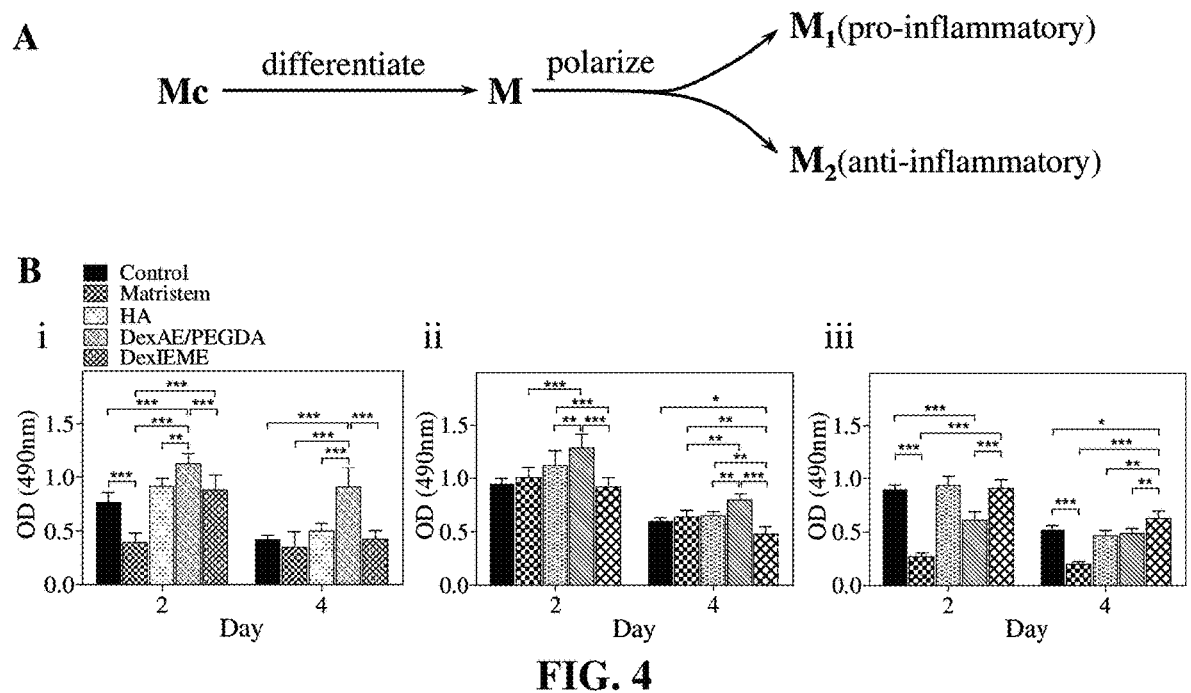
FIG. 4 shows the macrophage differentiation and polarization.
Figure 5:
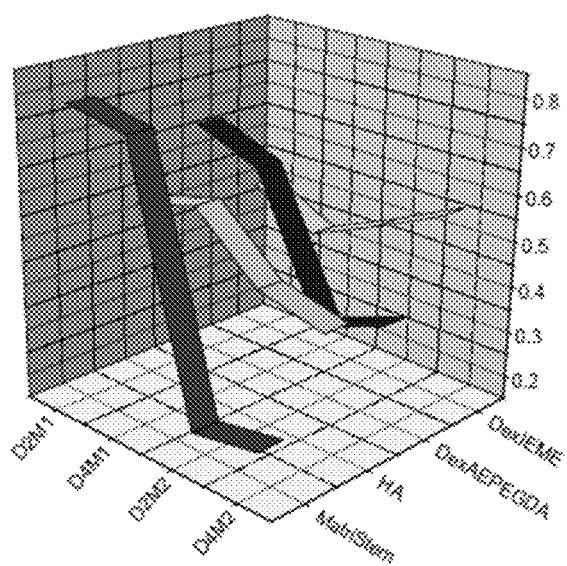
FIG. 5 illustrates the effect of macromers on the macrophage polarization into M1 and M2. DexIEME induces lower pro-inflammatory M1 but promotes higher anti-inflammatory M2 macrophage phenotype.

Excessive inflammatory cells result in fibrosis tissue formation in adults. Consequently, a scaffold that causes no or less immune response is especially desirable for wound healing. Macrophage differentiation and polarization were shown in FIG. 4. FIG. 4B(i) revealed that DexIEME has significantly lower inflammatory response in 4 days than Dex-AE when exposed to macrophage. Further study also revealed that DexIEME cause less pro-inflammatory response than Dex-AE, HA and MatriStem (FIG. 4B(ii)), but showed greater anti-inflammatory responses (FIG. 4B(iii)). As shown in FIG. 5, MatriStem has a robust pro-inflammatory response, while DexIEME has lower pro-inflammatory response but strong anti-inflammatory response. Collectively, such results clearly indicate that DexIEME causes low immune response and could be a good candidate for skin regeneration. Along with cytotoxicity, its safety is further substantiated.

Example 4

Preparation of Bioabsorbable Dex Hydrogels

DexIEME hydrogels were prepared similar to as previously reported (Sun et al., Carbohydrate Polymers, Vol. 65, pp. 273-287 (2006)). DexIEME was dissolved at different concentrations (e.g., 10%) into phosphate buffered saline (PBS) containing 0.1% (w/w) 2-methyl-1-[4-(hydroxyethoxy)phenyl]-2-methyl-1-propanone (Irgacure 2959, Ciba). The mixture was pipetted into a mold (e.g., 100 µL volume per mold) to obtain discs after photo-polymerizing. The resulting hydrogels were removed from the mold and immersed in sterile PBS solution before application onto wounds.

Hydrogel Conversion Efficiency

The hydrogel precursors react with each other to form three-dimensional networks, and their conversion efficiency was estimated from the following equation: conversion efficiency (%)=$W_d/W_o \times 100$, where $W_d$ is the weight of dried hydrogel after being washed with distilled water and $W_o$ is the initial precursor weight.

Swelling Test

The swelling property of the hydrogels was determined as previously reported (Sun et al. Carbohydrate Polymers, Vol. 65, pp. 273-287, 2006). The swelling ratio was calculated according to the formula below: swelling ratio (%)=$[(W_s - W_d)/W_d] \times 100$, where $W_d$ is the weight of dry hydrogel specimens, and $W_s$ is weight of swollen hydrogels at predetermined intervals at room temperature (25° C.). The hydrogel reached an equilibrium swelling state when there was no difference in swelling ratio between two adjacent intervals.

Figure 7:
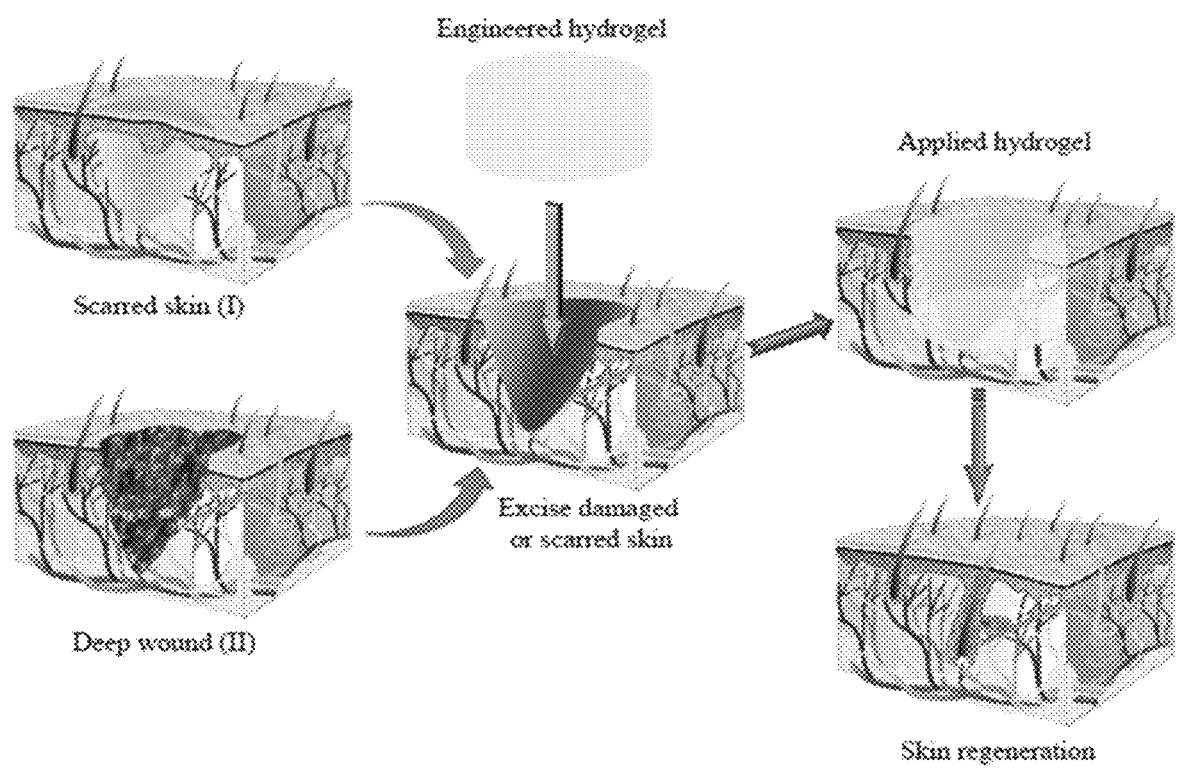
FIG. 7 illustrates intelligent hydrogels as regenerative therapies for acute skin injuries and abnormal wound healings. To manipulate wound healing to become more regenerative instead of repairing, biomimetic scaffolds that can establish key interactions with cells in ways that unlock the body's innate powers of regeneration are developed. Either acute deep injuries (I) or scarred skins (II) are excised first, and instructive hydrogels that can trigger, activate different signaling pathways and instruct endogenous stem cells to proliferate, differentiate, migrate are then applied to injured sites, so that skin stem cells can self-assemble into complete skin structures.

In some embodiments, the hydrogel or the composition (either solid or fluid-like) is administered to at least part of the injured area. In some embodiments, a pre-formed hydrogel is placed on the injured area. In one embodiment, the hydrogel is formed in any shape, including, but not limited to, ovoid, sphere, disc, sheet or other structure. In one embodiment, the shape of the hydrogel depends on the wound shape, and the hydrogel can be either pre-shaped or cut to fit the wound. In some embodiments, the hydrogel may be photo-crosslinked on the injured site. In some embodiments, the hydrogel may be administered to extend the hydrogel over an uninjured area, in addition to the injured area. In some embodiments, the entire injured area may be covered by the hydrogel, with or without extension over an uninjured area. Such administration is illustrated in FIG. 7.

Example 5

Surgery Procedure

Animal care and surgery were performed according to approved protocols and in conformity with the NIH guidelines (NIH publication #85-23, revised 1985). To examine therapeutic capacity of our hydrogel on damaged skin, a pre-formed scarring skin was first generated on mice by third-degree burn injury. The burn injury was performed as previously reported (Sun et al. Proc Natl Acad Sci USA, Vol. 108, pp. 20976-20981, 2011; Zhang et al. Arch Surg, Vol. 145, pp. 259-266, 2010). Briefly, mice were first anesthetized; then the dorsum were shaved and cleaned with alcohol. A 1.2-cm-diameter third-degree burn was then generated. The burned injuries healed by themselves and scarred skins were then formed in 5 weeks. Full or nearly half of full thick scarred skin was exercised, and the wounds were covered with the same size of DexIEME hydrogel and further covered with appropriate dressing.

To further investigate the regenerative effect of the hydrogel on healing larger wounds, 2.5 cm (or 1 inch) diameter wounds down to subcutaneous tissue were created on the dorsum of 3-month Bahamas mini pigs. The wounds were covered with the same size of the hydrogels and further covered with appropriate dressing. To protect the hydrogels and dressings from being damaged or lost, additional layers of blankets were wrapped up around the body.

Histology

DexIEME hydrogel explants were fixed with 10% formaldehyde solution for 24 hours, dehydrated in graded ethanol (70 to 100%), embedded in paraffin, followed by a series of five-micrometer thick sections, and then stained with either hematoxylin and eosin (H&E) or immunohistochemistry for skin structures.

Figure 8:
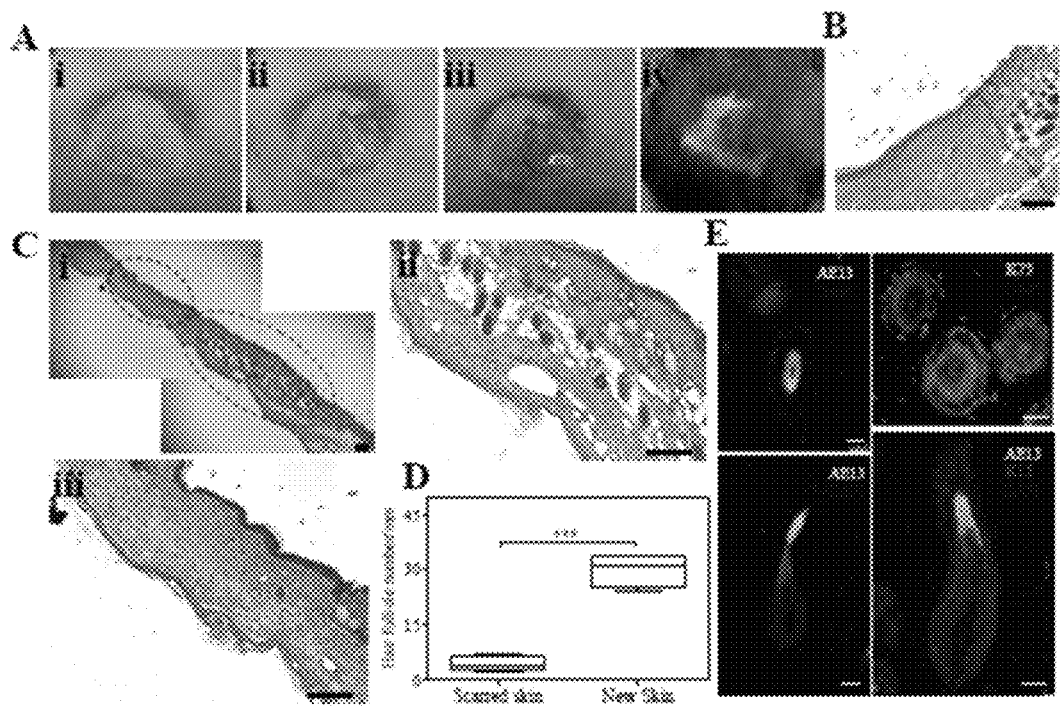
FIG. 8 exemplifies hydrogel treatment for pre-existing scars.

The hydrogel was used to treat pre-existing scars (FIG. 8). As shown in FIG. 8A, scarred skin was created and partially treated with hydrogel in mouse dorsum. The scar was created by third-degree burns and the scarred skin was partially excised (FIG. 8A (i) and (ii) and FIG. 8B). Hydrogel was applied to the wounded area (FIG. 8A(iii)) with the outcome shown in FIG. 8A(iv). FIG. 8B shows the outcome of the wound healing after 5 weeks of third-degree burn. In FIG. 8C, the newly regenerated skin was shown after hydrogel treatment. The representative hematoxylin and eosin (H&E) was used to stain the newly regenerated skin from the scar, while the dotted lines delineate the scarred skin caused by burns and the newly regenerated skin after hydrogel treatment (FIG. 8C(i)). FIG. 8C(ii) shows the higher magnification of completely regenerated skin from the scar site. FIG. 8C(iii) shows the higher magnification of scarred skin caused by burns remains unchanged. The regenerated skin shows skin appendages and subcutaneous tissue, while the original scarred skin caused by burns still remains as scarred skin. FIG. 8D shows the number of hair follicles between the newly regenerated skin and scarred skin. FIG. 8E shows the newly regenerated hair expressed in cortex (AE13), companion layer (k75) and outer root sheath (AE13/AE15).

Figure 9:
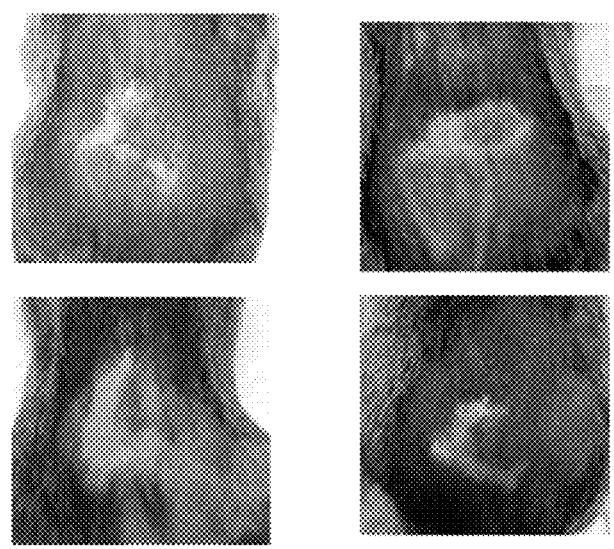
FIG. 9 shows the partial treatment of scarred skin. New skin regenerated after DexIEME treatment.

FIG. 9 exemplifies hydrogel treatment for pre-existing scars. FIG. 8D was calculated based on the HE image obtained from these experiments.

Figure 10:
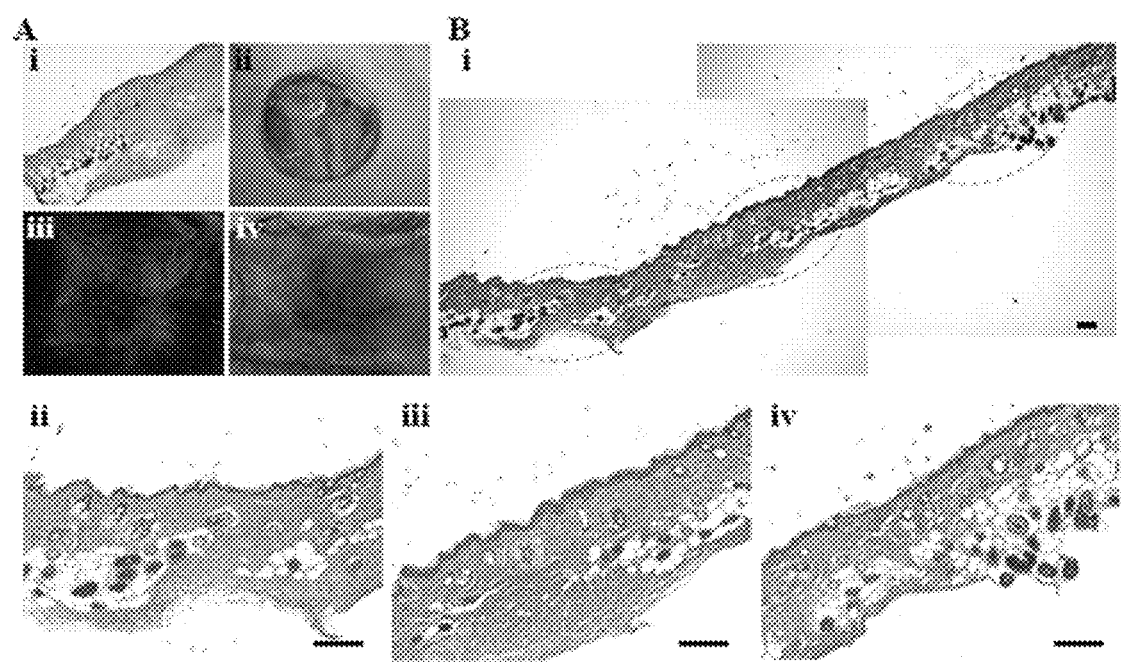
FIG. 10 shows further hydrogel treatment for full pre-existing scars.

FIG. 10 shows further hydrogel treatment for full pre-existing scars. FIG. 10A shows the creation of scarred skin and full scar removal and subsequent hydrogel treatment in mouse dorsum. FIG. 10A(i) is the skin excised from burn wounds, while FIG. 10A(ii) shows the full coverage with DexIEME after scarred skin was removed, while FIGS. 10A(iii) and 10A(iv) show both sides of the newly regenerated skin. FIG. 10B shows hydrogel regenerating a complete skin structure. FIG. 10B(i) shows regenerated skin from the scar, while the dotted lines delineate the new skin from three different locations, while FIGS. 10B(i), 10B(ii), and 10B(iii) are the blow-up of the three locations indicating new skin formation.

Taken together, both partial treatment and full treatment of third-degree burn scars with DexIEME hydrogel regenerated new skin.

Figure 11:
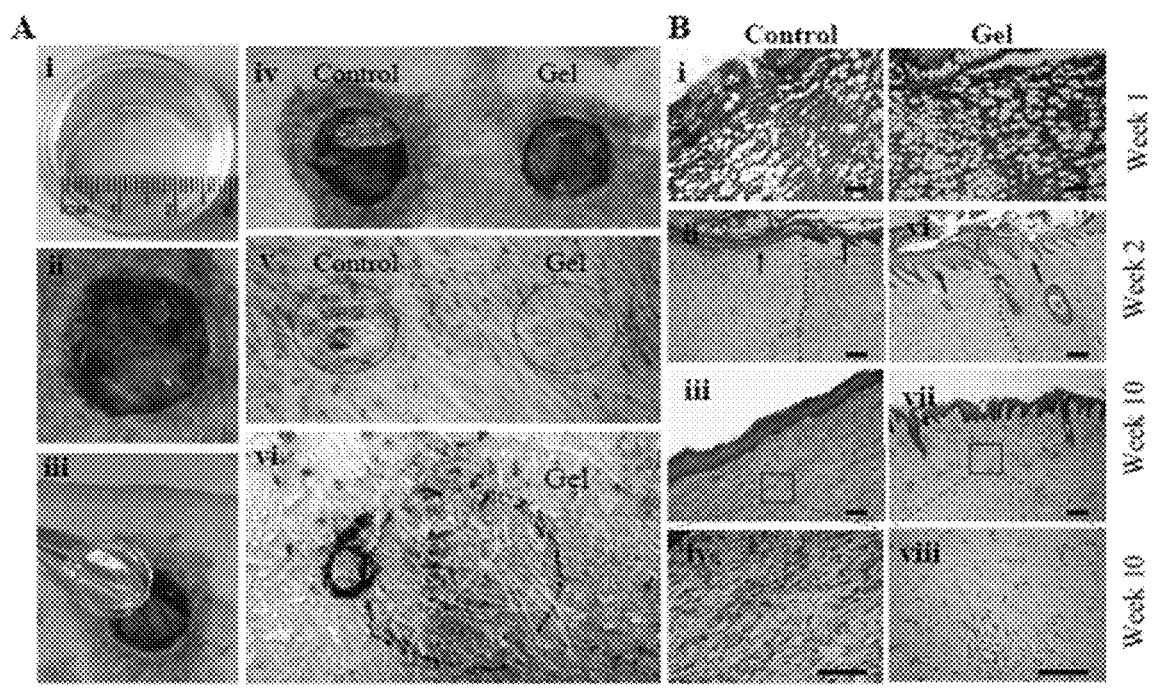
FIG. 11 shows hydrogel healed acute deep wound on pig.
Figure 12:
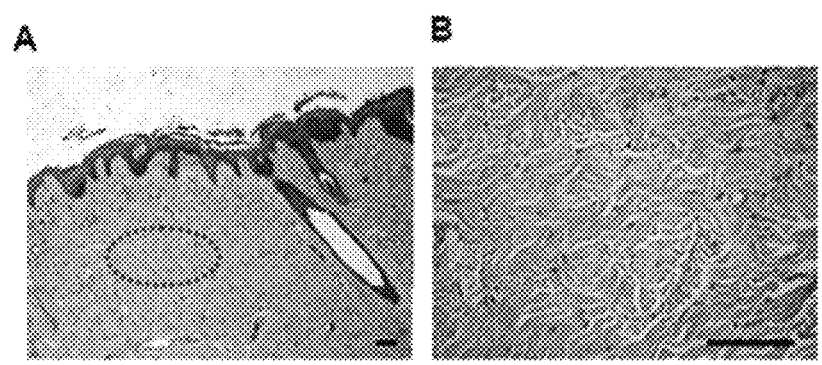
FIG. 12 exemplifies normal porcine skin. (A) H&E-stained histologic sections of normal porcine skin structures and (B) its dermal layer structure at higher magnification. Scale bars=100 µm.

To further demonstrate the efficiency of DexIEME hydrogel, a preclinical pig model is employed. FIG. 11 shows hydrogel healed acute deep wounds on a pig. FIG. 11A shows the surgical procedure of a full skin excision down to subcutaneous tissue followed by hydrogel treatment for up to 10 weeks. FIG. 11B shows the representative H&E images of wound healing at different time points: (i) (ii) and (iii) are the wound without hydrogel treatment, (v)(vi) and (vii) are the wound with hydrogel treatment, (iv) and (viii) are blow-ups of the control and hydrogel-treated wounds, respectively. The dotted line in FIGS. 11B(ii) and 11B(vi) delineates the wound interface between the newly formed tissue and normal skin. Compared to normal pig skin in FIG. 12, a complete skin structure was formed after 10 weeks of DexIEME hydrogel treatment.

EQUIVALENTS

It is to be understood that while the disclosure has been described in conjunction with the above embodiments, the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs.

The embodiments illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement, and variation of the embodiments therein herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A composition comprising a polysaccharide which comprises a first repeat unit and a second repeat unit,
wherein the first repeat unit has formula (I):

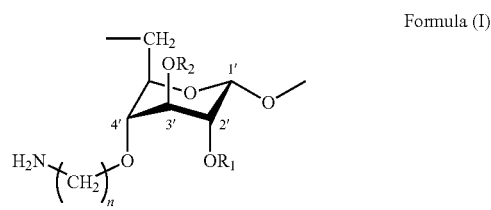

Formula (I)

wherein the second repeat unit has formula (II):

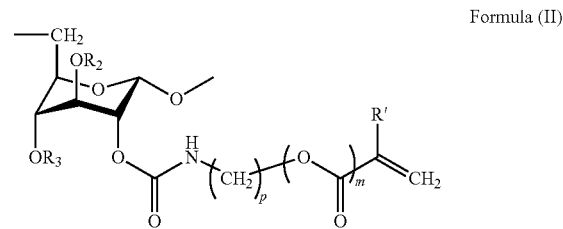

Formula (II)

wherein R1 is selected from the group consisting of hydrogen, —OCONH(CH$_2$)$_p$(COO)$_m$CR'=CH$_2$, and —O(CH$_2$)$_n$NH$_2$, wherein R' is hydrogen or a methyl group, n is no less than 1, m is no less than 1, and p is no less than 1;

wherein R2 is selected from the group consisting of hydrogen, —OCONH(CH$_2$)$_p$(COO)$_m$CR'=CH$_2$, and —O(CH$_2$)$_n$NH$_2$, wherein R' is hydrogen or a methyl group, n is no less than 1, m is no less than 1, and p is no less than 1;

wherein R3 is selected from the group consisting of hydrogen, —OCONH(CH$_2$)$_p$(COO)$_m$CR'=CH$_2$, and —O(CH$_2$)$_n$NH$_2$, wherein R' is hydrogen or a methyl group, n is no less than 1, m is no less than 1, and p is no less than 1.

2. The composition of claim 1, wherein the polysaccharide has formula (III):

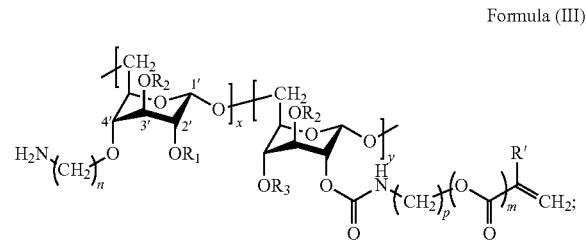

Formula (III)

wherein x is more than 1 and y is more than 1.

3. The composition of claim 1 or 2, wherein p=2.

4. The composition of claim 1, wherein m=1.

5. The composition of claim 1, wherein R' is a methyl group.

6. The composition of claim 1, wherein n=2 or 3.

7. The composition of claim 1, wherein —O(CH$_2$)$_n$NH$_2$ is formula (IV):

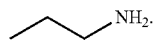

Formula (IV)

8. The composition of claim 1, wherein —O(CH$_2$)$_n$NH$_2$ has formula (V):

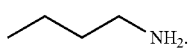

Formula (V)

9. The composition of claim 1, wherein —OCONH(CH$_2$)$_p$(COO)$_m$CR'=CH$_2$ has formula (VI):

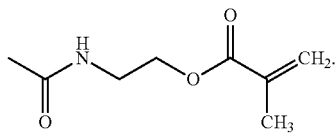

Formula (VI)

10. The composition of claim 1, wherein R1 is formula IV, R2 is hydrogen or formula VI, and R3 is hydrogen or formula VI;
wherein R1 is hydrogen or formula VI, R2 is formula IV, and R3 is hydrogen or formula VI;
wherein R1 is hydrogen or formula VI, R2 is hydrogen or formula VI, and R3 is formula IV;
wherein R1 is formula IV, R2 is formula IV or formula VI, and R3 is formula IV or formula VI, or
wherein R1 is formula VI, R2 is formula IV, and R3 is formula IV.

11. The composition of claim 1, wherein R1 has formula V, R2 is hydrogen or formula VI, and R3 is hydrogen or formula VI;
wherein R1 is hydrogen or formula VI, R2 is formula V, and R3 is hydrogen or formula VI;
wherein R1 is hydrogen or formula VI, R2 is hydrogen or formula VI, and R3 is formula V;
wherein R1 is formula V, R2 is formula V or formula VI, and R3 is formula V or formula VI; or
wherein R1 is formula VI, R2 is formula V, and R3 is formula V.

12. The composition of claim 1, wherein the polysaccharide comprises dextran.

13. The composition of claim 12, wherein the dextran has more than 13 repeat units.

14. The composition of claim 12, wherein the dextran has 10, 100, 500, 10$^4$, or more than 10$^4$ repeat units.

15. The composition of claim 1, wherein the repeat unit comprises an amine group.

16. The composition of claim 1, wherein the polysaccharide comprises at least one hydrolytically degradable moiety, wherein the hydrolytically degradable moiety is disposed between the biocompatible glucose repeat unit and a crosslinking group.

17. The composition of claim 16, wherein the crosslinking group comprises an unsaturated vinyl group.

18. The composition of claim 16, wherein the hydrolytically degradable moiety comprises an ester group.

19. The composition of claim 15, wherein the amine group comprises a primary amine group.

20. The composition of claim 1, wherein the amine group and the crosslinking group may be on the same or different repeat units.

21. The composition of claim 1, wherein the polysaccharide is crosslinked.

22. The composition of claim 1, wherein the composition is a hydrogel.

23. The composition of claim 1, wherein the composition further comprises a bioactive agent.

24. The composition of claim 23, wherein the bioactive agent is selected from the group consisting of pharmaceutical agents, drugs, cells, gases and gaseous precursors, synthetic organic molecules, proteins, enzymes, growth factors, vitamins, steroid, polyanions, nucleosides, nucleotides, polynucleotides, nanoparticles, diagnostic agents, genetic materials, and any combinations thereof.

25. The composition of claim 24, wherein the growth factor is selected from the group consisting of epidermal growth factor, platelet derived growth factor, hepatocytic growth factor, human growth hormone, fibroblast growth factor, vascular endothelium growth factor and combinations thereof.

26. The composition of claim 1, wherein the degree of substituted hydroxyl group of OCONH(CH$_2$)$_p$(COO)$_m$CR'=CH$_2$ on the polysaccharide is from 0.05 to 0.97.

27. The composition of claim 1, wherein the degree of substituted hydroxyl group of —O(CH$_2$)$_n$NH$_2$ on the polysaccharide is from 0.03 to 0.95.

28. A method of forming the composition of claim 1 into a hydrogel, comprising:
combining in a solution the composition of claim 1 for a sufficient period of time; and
exposing the solution to UV light, wherein a crosslinked polymer network structure is formed within the composition after exposure.

29. The method of claim 28, further comprising casting the hydrogel composition into a predetermined cast shape.

30. The method of claim 28, further comprising: cutting, folding, stretching, coring, and/or machining the composition to a predetermined shape or dimension that is different from the cast shape.

31. A method of synthesizing a macromer, comprising:
reacting a first compound comprising —(CH$_2$)$_p$(COO)$_m$CR'=CH$_2$ with a hydroxyl group of a polysaccharide to give rise to a first macromer comprising a polymerizing moiety and a hydrolytically degradable linker, where the macromer is formula II, and
reacting the first macromer with a second compound comprising —(CH$_2$)$_n$NH$_2$ with a free hydroxyl group of the first macromere to form a second macromere, wherein the second macromer is formula III.

32. The method of claim 31, wherein the hydroxyl group reacts with an isocyanate group to form a urethane group in presence of dibutyltin dilaurate, thus incorporating a biodegradable ester group and an unsaturated vinyl group into the polysaccharide.

33. The method of claim 31, wherein the hydroxyl group is substituted to give rise to a primary amine side group in presence of trimethylamine.

34. The method of claim 31, wherein the polysaccharide comprises dextran.

35. A hydrogel forming system, wherein the system consists essentially of a polysaccharide which comprises the first repeat unit of formula I and the second repeat unit of formula II, wherein at least one repeat unit having at least a polymerizing moiety;

wherein the system is polymerized after exposed to UV light, thus forming a three-dimensional polymer network.

36. The system of claim 35, wherein the hydrogel-forming system has a weight concentration from 0.01 to 99.99%.

37. The system of claim 36, wherein the hydrogel is capable of loading a protein molecule and releasing the molecule in a controlled manner.

38. A method of promoting cutaneous wound healing, the method comprising applying to a portion of injured skin area the composition of claim 1.

39. A method of promoting dermal regeneration and skin appendage, wherein the method comprises applying a portion of injured skin area the composition of claim 38.

40. The method of claim 39, wherein the skin appendage comprises hair follicle, sebaceous glands, and sweat glands.

41. The method of claim 38 or 39, wherein the injured skin area comprises a scratch, cut, tear, scrape, bruise abrasion, puncture, incision, first degree burn, second degree burn, third degree burn, open wound, skin avulsion, and/or laceration.

42. A method of attenuating scarring, wherein the method comprising:
excising the scarred skin, and
regenerating the skin on scarred skin area with the composition of claim 1.

43. The method of claim 39 or 42, wherein the composition is hydrogel.

44. The method of claim 43, wherein the hydrogel comprises liquid hydrogel, solid hydrogel, nanosized hydrogel, and/or macrosized hydrogel.

45. The method of claim 43, wherein the hydrogel can absorb excess fluid, exudate and/or retain moisture.

46. The method of claim 38 or 43, wherein the composition is applied to entire injured area.

47. The method of claim 38 or 43, where the composition comprises a bioactive agent to a subject in need of treatment.

48. The method of claim 47, wherein the bioactive agent comprises a medicament; vitamin, a mineral supplement, a pro-drug, a growth factor, or a pharmaceutically active agent.

49. The method of claim 43, wherein the hydrogel is used to regenerate new tissue or protect tissue from being further damaged or deteriorated.

50. The method of claim 49, wherein the tissue comprises skin, muscle, bone, liver, lung, skeletal muscle, dental pulp, vasculature, gastrointestinal tract, cardiac tissue, ocular tissue, gut, intervertebral disk, cartilage, ligament, tendon, or the combination thereof.

* * * * *